(12) United States Patent
Douglass et al.

(10) Patent No.: US 6,920,239 B2
(45) Date of Patent: Jul. 19, 2005

(54) METHOD AND APPARATUS FOR AUTOMATED IMAGE ANALYSIS OF BIOLOGICAL SPECIMENS

(75) Inventors: James W. Douglass, Indialantic, FL (US); Thomas J. Riding, West Melbourne, FL (US); James E. Ring, Melbourne Beach, FL (US)

(73) Assignee: ChromaVision Medical Systems, Inc., San Juan Capistrano, CA (US)

( * ) Notice: Subject to any disclaimer, the term of this patent is extended or adjusted under 35 U.S.C. 154(b) by 94 days.

(21) Appl. No.: 10/404,921

(22) Filed: Mar. 31, 2003

(65) Prior Publication Data

US 2003/0228038 A1 Dec. 11, 2003

Related U.S. Application Data

(63) Continuation of application No. 09/492,101, filed on Feb. 14, 2000, now Pat. No. 6,553,135, which is a continuation of application No. 08/758,436, filed on Nov. 27, 1996, now Pat. No. 6,215,892.
(60) Provisional application No. 60/026,805, filed on Nov. 30, 1995.

(51) Int. Cl.$^7$ .............................. G06K 9/00; G09G 5/02
(52) U.S. Cl. ....................................... 382/128; 345/604
(58) Field of Search ................................. 382/128–134, 382/162, 203, 165, 167, 279; 250/201.3; 436/46, 43; 356/23; 435/7.23; 345/582, 604; 422/63; 358/505, 515, 518

(56) References Cited

U.S. PATENT DOCUMENTS

| | | |
|---|---|---|
| 3,824,393 A | 7/1974 | Brain |
| 3,851,972 A | 12/1974 | Smith et al. |

(Continued)

FOREIGN PATENT DOCUMENTS

| | | |
|---|---|---|
| DE | 3340647 | 5/1985 |
| DE | 3735091 A1 | 4/1998 |
| EP | 0213666 | 3/1987 |
| EP | 0557871 | 9/1993 |
| EP | 0713086 A1 | 5/1996 |
| WO | 9217848 | 10/1992 |
| WO | 9720198 | 6/1997 |
| WO | 00/49391 | 8/2000 |
| WO | 01/37206 | 5/2001 |
| WO | 03/014795 | 2/2003 |

OTHER PUBLICATIONS

Baxes et al., "Digital Image Processing,", pp. 127–137.

(Continued)

Primary Examiner—Kanjibhai Patel
(74) Attorney, Agent, or Firm—Fish & Richardson P.C.

(57) ABSTRACT

A method and apparatus for automated cell analysis of biological specimens automatically scans at a low magnification to acquire images which are analyzed to determine candidate cell objects of interest. The low magnification images are converted from a first color space to a second color space. The color space converted image is then low pass filtered and compared to a threshold to remove artifacts and background objects from the candidate object of interest pixels of the color converted image. The candidate object of interest pixels are morphologically processed to group candidate object of interest pixels together into groups which are compared to blob parameters to identify candidate objects of interest which correspond to cells or other structures relevant to medical diagnosis of the biological specimen. The location coordinates of the objects of interest are stored and additional images of the candidate cell objects are acquired at high magnification. The high magnification images are analyzed in the same manner as the low magnification images to confirm the candidate objects of interest which are objects of interest. A high magnification image of each confirmed object of interest is stored for later review and evaluation by a pathologist.

6 Claims, 25 Drawing Sheets

U.S. PATENT DOCUMENTS

| | | | |
|---|---|---|---|
| 4,011,004 A | | 3/1977 | Levine et al. |
| 4,125,828 A | | 11/1978 | Resnick et al. |
| 4,196,265 A | | 4/1980 | Koprowski et al. |
| 4,210,419 A | * | 7/1980 | Castleman .................. 436/46 |
| 4,249,825 A | | 2/1981 | Shapiro |
| 4,338,024 A | * | 7/1982 | Bolz et al. .................... 356/23 |
| 4,393,466 A | | 7/1983 | Deindoerfer et al. |
| 4,513,438 A | | 4/1985 | Graham et al. |
| 4,612,614 A | | 9/1986 | Deindoerfer et al. |
| 4,656,594 A | | 4/1987 | Ledley |
| 4,673,973 A | | 6/1987 | Ledley |
| 4,700,298 A | | 10/1987 | Palcic et al. |
| 4,741,043 A | | 4/1988 | Bacus |
| 4,945,220 A | | 7/1990 | Mallory et al. |
| 4,965,725 A | | 10/1990 | Rutenberg |
| 4,991,223 A | | 2/1991 | Bradley |
| 5,003,165 A | | 3/1991 | Sarfati et al. |
| 5,008,185 A | | 4/1991 | Bacus |
| 5,016,173 A | | 5/1991 | Kenet et al. |
| 5,018,209 A | | 5/1991 | Bacus |
| 5,068,909 A | | 11/1991 | Rutherford et al. |
| 5,085,325 A | | 2/1992 | Jones et al. |
| 5,087,965 A | | 2/1992 | Torre-Bueno |
| 5,123,055 A | | 6/1992 | Kasdan |
| 5,202,931 A | | 4/1993 | Bacus |
| 5,231,580 A | | 7/1993 | Cheung et al. |
| 5,233,684 A | | 8/1993 | Ulichney et al. |
| 5,254,845 A | | 10/1993 | Burgess et al. |
| 5,257,182 A | | 10/1993 | Luck et al. |
| 5,268,966 A | | 12/1993 | Kasdan |
| 5,287,272 A | | 2/1994 | Rutenberg et al. |
| 5,317,140 A | | 5/1994 | Dunthorn |
| 5,321,545 A | | 6/1994 | Bisconte |
| 5,333,207 A | | 7/1994 | Rutenberg |
| 5,338,924 A | | 8/1994 | Barrett et al. |
| 5,352,613 A | | 10/1994 | Tafas et al. |
| 5,375,177 A | | 12/1994 | Vaidyanathan et al. |
| 5,409,007 A | | 4/1995 | Saunders et al. |
| 5,428,690 A | | 6/1995 | Bacus et al. |
| 5,432,871 A | | 7/1995 | Novik |
| 5,449,622 A | | 9/1995 | Yabe et al. |
| 5,459,385 A | | 10/1995 | Lipo et al. |
| 5,463,470 A | | 10/1995 | Terashita et al. |
| 5,469,353 A | | 11/1995 | Pinsky et al. |
| 5,473,706 A | | 12/1995 | Bacus et al. |
| 5,481,401 A | | 1/1996 | Kita et al. |
| 5,499,097 A | | 3/1996 | Ortyn et al. |
| 5,515,172 A | | 5/1996 | Shiau |
| 5,526,258 A | | 6/1996 | Bacus |
| 5,533,628 A | | 7/1996 | Tao |
| 5,583,666 A | | 12/1996 | Ellson et al. |
| 5,585,469 A | | 12/1996 | Kojima et al. |
| 5,586,160 A | | 12/1996 | Mascio |
| 5,602,941 A | | 2/1997 | Charles et al. |
| 5,619,032 A | * | 4/1997 | Kasdan .................. 250/201.3 |
| 5,625,705 A | | 4/1997 | Recht |
| 5,625,709 A | * | 4/1997 | Kasdan ...................... 382/203 |
| 5,635,402 A | | 6/1997 | Alfano et al. |
| 5,646,677 A | | 7/1997 | Reber |
| 5,647,025 A | | 7/1997 | Frost et al. |
| 5,671,288 A | | 9/1997 | Wilhem et al. |
| 5,690,892 A | | 11/1997 | Babler et al. |
| 5,691,779 A | | 11/1997 | Yamashita et al. |
| 5,701,172 A | | 12/1997 | Azzazy |
| 5,706,093 A | | 1/1998 | Komiya |
| 5,726,009 A | | 3/1998 | Connors et al. |
| 5,731,156 A | | 3/1998 | Golbus |
| 5,735,387 A | | 4/1998 | Polaniec et al. |
| 5,740,267 A | | 4/1998 | Echerer et al. |
| 5,740,270 A | | 4/1998 | Rutenberg et al. |
| 5,773,459 A | | 6/1998 | Tang et al. |
| 5,783,814 A | | 7/1998 | Fairley et al. |
| 5,795,723 A | | 8/1998 | Tapscott et al. |
| 5,799,105 A | | 8/1998 | Tao |
| 5,846,749 A | | 12/1998 | Slamon et al. |
| 5,854,851 A | | 12/1998 | Bamberger et al. |
| 5,867,598 A | | 2/1999 | de Queiroz |
| 5,877,161 A | | 3/1999 | Riabowol |
| 5,880,473 A | | 3/1999 | Ginestet |
| 5,888,742 A | | 3/1999 | Lal et al. |
| 5,889,881 A | | 3/1999 | MacAulay et al. |
| 5,911,003 A | | 6/1999 | Sones |
| 5,911,327 A | | 6/1999 | Tanaka et al. |
| 5,966,309 A | | 10/1999 | O'Bryan et al. |
| 5,966,465 A | | 10/1999 | Keith et al. |
| 6,006,191 A | | 12/1999 | DiRienzo |
| 6,007,996 A | | 12/1999 | McNamara et al. |
| 6,011,595 A | | 1/2000 | Henderson et al. |
| 6,031,929 A | | 2/2000 | Maitz et al. |
| 6,040,139 A | | 3/2000 | Bova |
| 6,058,322 A | | 5/2000 | Nishikawa et al. |
| 6,072,570 A | | 6/2000 | Chipman et al. |
| 6,097,838 A | | 8/2000 | Klassen et al. |
| 6,101,265 A | | 8/2000 | Bacus et al. |
| 6,117,985 A | | 9/2000 | Thomas et al. |
| 6,122,400 A | | 9/2000 | Reitmeier |
| 6,125,194 A | | 9/2000 | Yeh et al. |
| 6,141,602 A | | 10/2000 | Igarashi et al. |
| 6,151,535 A | | 11/2000 | Ehlers |
| 6,169,816 B1 | | 1/2001 | Ravkin |
| 6,215,892 B1 | | 4/2001 | Douglass et al. |
| 6,215,894 B1 | | 4/2001 | Zeleny et al. |
| 6,225,636 B1 | | 5/2001 | Ginestet |
| 6,226,392 B1 | | 5/2001 | Bacus et al. |
| 6,236,031 B1 | | 5/2001 | Ueda |
| 6,238,892 B1 | | 5/2001 | Mercken et al. |
| 6,259,807 B1 | | 7/2001 | Ravkin |
| 6,290,907 B1 | | 9/2001 | Takahashi et al. |
| 6,313,452 B1 | | 11/2001 | Paragano et al. |
| 6,374,989 B1 | | 4/2002 | Van Dyke, Jr. et al. |
| 6,418,236 B1 | | 7/2002 | Ellis et al. |
| 6,466,690 B2 | | 10/2002 | Bacus et al. |
| 6,518,554 B1 | | 2/2003 | Zhang |
| 6,553,135 B1 | | 4/2003 | Douglass et al. |
| 6,631,203 B2 | | 10/2003 | Ellis et al. |
| 6,671,393 B2 | | 12/2003 | Hays et al. |
| 6,674,896 B1 | | 1/2004 | Torre-Bueno |
| 6,697,509 B2 | | 2/2004 | De La Torre-Bueno |
| 6,718,053 B1 | | 4/2004 | Ellis et al. |
| 2002/0067409 A1 | | 6/2002 | Harari et al. |
| 2002/0164810 A1 | | 11/2002 | Dukor et al. |
| 2003/0124589 A1 | | 7/2003 | Piper |
| 2003/0170703 A1 | | 9/2003 | Piper et al. |

OTHER PUBLICATIONS

Simpson et al., "Isolating Fetal Cells From Maternal Blood—Advances in Prenatal Diagnosis Through Molecular Technology", *JAMA,* vol. 270, No. 19, pp. 2357–2361 (Nov. 17, 1993).

Price, J.O., et al., "Prenatal Diagnosis with Fetal Cells Isolated From Maternal Blood by Multiparameter Flow Cytometry," *AM. J. Obster. Gynecol.,* vol. 165, pp. 1731–1737 (Dec. 1991).

Mansi, J.L. et al., "Bone Marow Micrometastases in Primary Breast Cancer: Prognosis Significance After 6 Years' Follow–Up," *Eur. J. Cancer,* vol. 27, No. 12, pp. 1552–1555 (1991).

Cote, R.J. et al., "Prediction of Early Relapse in Patients with Operable Breast Cancer by Detection Occult Bone Marrow Micrometastases," *Journal of Clinical Oncology*, vol. 9, No. 10, pp. 1749–1756, (Oct. 1991).

Moss, T.J. et al., "Prognostic Value of Immunocytologic Detection of Bone Marrow Metastases in Neuroblastoma," *The New England Journal of Medicine*, vol. 324, No. 4, pp. 219–226 (Jan. 1991).

McKeough et al., "A low–cost automatic translation and autofocusing system for a microscope", *Meas. Sci. Technol.*, 6, (1995), pp. 583–587.

Aziz, Douglas C., "Quantitation of Estrogen and Progesterone Receptors by Immunocytochemical and Image Analyses", Anatomic Pathology, From Cytometrics, Inc., Division of Specialty Laboratories, pp. 105–111, Jul. 1991.

Bacus S. et al., "The Evaluation of Estrogen Receptor in Primary Breast Carcinoma by Computer–Assisted Image Analysis", American Journal of Clinical Pathology, vol. 90, No. 2, Aug. 1988, pp. 233–239.

Baddoura, Fady K. et al., "Image Analysis for Quantitation of Estrogen Receptor in Formalin–Fixed Paraffin–Embedded Sections of Breast Carcinoma", Modern Pathology, vol. 4, No. 1, 1991, pp. 91–95.

Ballard, D.H., et al. Computer Vision *Prentice–Hall, Inc.,* Englewood Cliffs, NJ 07632 pp. 65–70 and 149–165 (1982).

Bander, N.H., Monoclonal antibodies to renal cancer antigens, vol. 18, Supp. 2, pp. 10–12, 1990. Abstract.

Caulet S. et al., "Comparative Quantitative Study of Ki–67 Antibody Staining in 78 B and T Cell Malignant Lymphoma (ML) Using Two Image Analyser Ssystems", Path. Res. Pract. 188, 490–496 (1992).

Diamond, David A. et al., "Computerized Image Analysis of Nuclear Shape as a Prognostic Factor for Prostatic Cancer", The Prostate 3:321–332 (1982).

Drobnjak, M. et al., "Immunocytochemical, Detection of Estrogen and Progesterone Receptors (ER/PR) in Paraffin Sections of Human Breast Cancinoma. Correlation with Biochemical Analysis and Automated Imaging Quantitation" Journal of the Academy of Pathology, vol. 64, No. 1, Jan. 1991. Abstract.

Duda R.O., et al. Pattern Classification and Scene Analysis *J. Wiley & Sons, Inc.* pp. 228–239 and 276–284 (1973).

Enestrom, Sverker et al., "Quantitative Ultrastructural Immunocytochemistry Using a Computerized Image Analysis System", Stain Technology, vol. 65, No. 6, pp. 263–278, 1990.

Esteban, J.M. et al., "Quantification of Estrogen Receptors on Paraffin–Embedded Tumors by Image Analysis", Modern Pathology, vol. 4, No. 1, pp. 53–57.

Goldschmidt, R.A. et al., "Automated Immunohistochemical Estrogen Receptor Staining and Computerized Image Analysis–Comparison with Biochemical Methods", Supplied by the British Library—"The world's knowledge" www.bl.uk.

Gross, Douglas S. et al., "Quantitative Immunocytochemistry of Hypothalamic and Pituitary Hormones: Validation of an Automated, Computerized Image Analysis Systems", The Journal of Histochemistry and Cytochemistry, vol. 33, No. 1, pp. 11–20, 1985.

Horsfall, D.J. et al., "Immunocytochemical assay for oestrogen receptor in fine needle aspirates of breast cancer by video image analysis", Br. J. Cancer (1989), 59, 129–134.

Kerns, B.J. et al., "Estrogen receptor status evaluated in formalin–fixed paraffin embedded breast carcinomas determined by automated immunohistochemistry and image analysis", Proceedings of the American Association for Cancer Research, vol. 35, Mar. 1994.

Levine, Gary M. et al., "Quantitative Immunocytochemistry by Digital Image Analysis: Application to Toxicologic Pathology", XICOLOGIC Pathology ISSN:0192–6233, vol. 15, No. 3, pp. 303–307, 1987.

Maudelonde, T. et al., "Immunostaining of Cathepsin D in Breast Cancer: Quantification by Computerised Image Analysis and Correlation with Cytosolic Assay", Eur T Cancer, vol. 28A, No. 10, pp. 1686–1691, 1992.

McClelland, Richard A. et al., "Automated Quantitation of Immunocytochemically Localized Estrogen Receptors in Human Breast Cancer", Cancer Research 50, 3545–3550, Jun. 1990.

McClelland, Richard A., et al., "A Multicentre Study into the Reliability of Steroid Receptor Immunocytochemical Assay Quantification", The European Journal of Cancer, vol. 27, No. 6, Jun. 1991, pp. 711–715.

Mize, R. Ranney et al., "Quantitative immunocytochemistry using an image analyzer. I. Hardware evaluation, image processing, and data analysis", Journal of Neuroscience Methods, 26 (1988) 1–24.

Press, Michael F. et al., "Her–2/*nue* Expression in Node–negative Breast Cancer: Direct Tissue Quantitation by Computerized Image Analysis and Association of Overexpression with Increased Risk of Recurrent Disease", Cancer Research 53, 4960–4970, Oct. 1993.

Roca et al., "New Autofocusing Algorithm for Cytological Tissue in a Microscopy Environment", Optical Engineering, Soc. of Photo–Optical Instrumentation Engineers, Bellingham, US, vol. 37, No. 2, pp. 635–641, Feb. 1, 1998.

Schultz, Daniel S., et al., "Comparison of Visual and CAS–200 Quantitation of Immunocytochemical Staining in Breast Carcinoma Samples", Analytical and Quantitative Cytology and Histology, vol. 14, No. 1, Feb. 1992.

Unnerstall, James R. et al., "New Approaches to Quantitative Neuropathology: Multtivariate Analysis of Morphologic and Neurochemical Measures", Neurobiology of Aging, vol. 8, pp. 567–569, Pergamon Journals Ltd., 1987.

\* cited by examiner

METHOD AND APPARATUS FOR AUTOMATED IMAGE ANALYSIS OF BIOLOGICAL SPECIMENS

This application is a continuation of U.S. patent application Ser. No. 09/492,101, filed Feb. 14, 2000, now U.S. Pat. No. 6,553,135 which is a continuation of U.S. patent application Ser. No. 08/758,436, filed Nov. 27, 1996, now U.S. Pat. No. 6,215,892, which claims the benefit of U.S. Provisional Application No. 60/026,805, filed Nov. 30, 1995.

BACKGROUND OF THE INVENTION

In the field of medical diagnostics including oncology, the detection, identification, quantitation and characterization of cells of interest, such as cancer cells, through testing of biological specimens is an important aspect of diagnosis. Typically, a biological specimen such as bone marrow, lymph nodes, peripheral blood, cerebrospinal fluid, urine, effusions, fine needle aspirates, peripheral blood scrapings or other materials are prepared by staining the specimen to identify cells of interest. One method of cell specimen preparation is to react a specimen with a specific probe which can be a monoclonal antibody, a polyclonal antiserum, or a nucleic acid which is reactive with a component of the cells of interest, such as tumor cells. The reaction may be detected using an enzymatic reaction, such as alkaline phosphatase or glucose oxidase or peroxidase to convert a soluble colorless substrate to a colored insoluble precipitate, or by directly conjugating a dye to the probe.

Examination of biological specimens in the past has been performed manually by either a lab technician or a pathologist. In the manual method, a slide prepared with a biological specimen is viewed at a low magnification under a microscope to visually locate candidate cells of interest. Those areas of the slide where cells of interest are located are then viewed at a higher magnification to confirm those objects as cells of interest, such as tumor or cancer cells. The manual method is time consuming and prone to error including missing areas of the slide.

Automated cell analysis systems have been developed to improve the speed and accuracy of the testing process. One known interactive system includes a single high power microscope objective for scanning a rack of slides, portions of which have been previously identified for assay by an operator. In that system, the operator first scans each slide at a low magnification similar to the manual method and notes the points of interest on the slide for later analysis. The operator then stores the address of the noted location and the associated function in a data file. Once the points of interest have been located and stored by the operator, the slide is then positioned in an automated analysis apparatus which acquires images of the slide at the marked points and performs an image analysis.

SUMMARY OF THE INVENTION

A problem with the foregoing automated system is the continued need for operator input to initially locate cell objects for analysis. Such continued dependence on manual input can lead to errors including cells of interest being missed. Such errors can be critical especially in assays for so-called rare events, e.g., finding one tumor cell in a cell population of one million normal cells. Additionally, manual methods can be extremely time consuming and can require a high degree of training to properly identify and/or quantify cells. This is not only true for tumor cell detection, but also for other applications ranging from neutrophil alkaline phosphatase assays, reticulocyte counting and maturation assessment, and others. The associated manual labor leads to a high cost for these procedures in addition to the potential errors that can arise from long, tedious manual examinations. A need, exists, therefore, for an improved automated cell analysis system which can quickly and accurately scan large amounts of biological material on a slide. Accordingly, the present invention provides a method and apparatus for automated cell analysis which eliminates the need for operator input to locate cell objects for analysis.

In accordance with the present invention, a slide prepared with a biological specimen and reagent is placed in a slide carrier which preferably holds four slides. The slide carriers are loaded into an input hopper of the automated system. The operator may then enter data identifying the size, shape and location of a scan area on each slide, or, preferably, the system automatically locates a scan area for each slide during slide processing. The operator then activates the system for slide processing. At system activation, a slide carrier is positioned on an X-Y stage of an optical system. Any bar codes used to identify slides are then read and stored for each slide in a carrier. The entire slide is rapidly scanned at a low magnification, typically 10×. At each location of the scan, a low magnification image is acquired and processed to detect candidate objects of interest. Preferably, color, size and shape are used to identify objects of interest. The location of each candidate object of interest is stored.

At the completion of the low level scan for each slide in the carrier on the stage, the optical system is adjusted to a high magnification such as 40× or 60×, and the X-Y stage is positioned to the stored locations for the candidate objects of interest on each slide in the carrier. A high magnification image is acquired for each candidate object of interest and a series of image processing steps are performed to confirm the analysis which was performed at low magnification. A high magnification image is stored for each confirmed object of interest. These images are then available for retrieval by a pathologist or cytotechnologist to review for final diagnostic evaluation. Having stored the location of each object of interest, a mosaic comprised of the candidate objects of interest for a slide may be generated and stored. The pathologist or cytotechnologist may view the mosaic or may also directly view the slide at the location of an object of interest in the mosaic for further evaluation. The mosaic may be stored on magnetic media for future reference or may be transmitted to a remote site for review and/or storage. The entire process involved in examining a single slide takes on the order of 2–15 minutes depending on scan area size and the number of detected candidate objects of interest.

The present invention has utility in the field of oncology for the early detection of minimal residual disease ("micrometastases"). Other useful applications include prenatal diagnosis of fetal cells in maternal blood and in the field of infectious diseases to identify pathogens and viral loads, alkaline phosphatase assessments, reticulocyte counting, and others.

The processing of images acquired in the automated scanning of the present invention preferably includes the steps of transforming the image to a different color space; filtering the transformed image with a low pass filter; dynamically thresholding the pixels of the filtered image to suppress background material; performing a morphological function to remove artifacts from the thresholded image; analyzing the thresholded image to determine the presence of one or more regions of connected pixels having the same color; and categorizing every region having a size greater than a minimum size as a candidate object of interest.

According to another aspect of the invention, the scan area is automatically determined by scanning the slide; acquiring an image at each slide position; analyzing texture information of each image to detect the edges of the specimen; and storing the locations corresponding to the detected edges to define the scan area.

According to yet another aspect of the invention, automated focusing of the optical system is achieved by initially determining a focal plane from an array of points or locations in the scan area. The derived focal plane enables subsequent rapid automatic focusing in the low power scanning operation. The focal plane is determined by determining proper focal positions across an array of locations and performing an analysis such as a least squares fit of the array of focal positions to yield a focal plane across the array. Preferably, a focal position at each location is determined by incrementing the position of a Z stage for a fixed number of coarse and fine iterations. At each iteration, an image is acquired and a pixel variance or other optical parameter about a pixel mean for the acquired image is calculated to form a set of variance data. A least squares fit is performed on the variance data according to a known function. The peak value of the least squares fit curve is selected as an estimate of the best focal position.

In another aspect of the present invention, another focal position method for high magnification locates a region of interest centered about a candidate object of interest within a slide which were located during an analysis of the low magnification images. The region of interest is preferably n columns wide, where n is a power of 2. The pixels of this region are then processed using a Fast Fourier Transform to generate a spectra of component frequencies and corresponding complex magnitude for each frequency component. Preferably, the complex magnitude of the frequency components which range from 25% to 75% of the maximum frequency component are squared and summed to obtain the total power for the region of interest. This process is repeated for other Z positions and the Z position corresponding to the maximum total power for the region of interest is selected as the best focal position. This process is preferably used to select a Z position for regions of interest for slides containing neutrophils stained with Fast Red to identify alkaline phosphatase in cell cytoplasm and counterstained with hemotoxylin to identify the nucleus of the neutrophil cell. This focal method may be used with other stains and types of biological specimens, as well.

According to still another aspect of the invention, a method and apparatus for automated slide handling is provided. A slide is mounted onto a slide carrier with a number of other slides side-by-side. The slide carrier is positioned in an input feeder with other slide carriers to facilitate automatic analysis of a batch of slides. The slide carrier is loaded onto the X-Y stage of the optical system for the analysis of the slides thereon. Subsequently, the first slide carrier is unloaded into an output feeder after automatic image analysis and the next carrier is automatically loaded.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The above and other features of the invention including various novel details of construction and combinations of parts will now be more particularly described with reference to the accompanying drawings and pointed out in the claims. It will be understood that the particular apparatus embodying the invention is shown by way of illustration only and not as a limitation of the invention. The principles and features of this invention may be employed in varied and numerous embodiments without departing from the scope of the invention.

FIG. 6b is a bottom view of the slide carrier of FIG. 6a.

DETAILED DESCRIPTION OF THE PREFERRED EMBODIMENT

Figure 1:
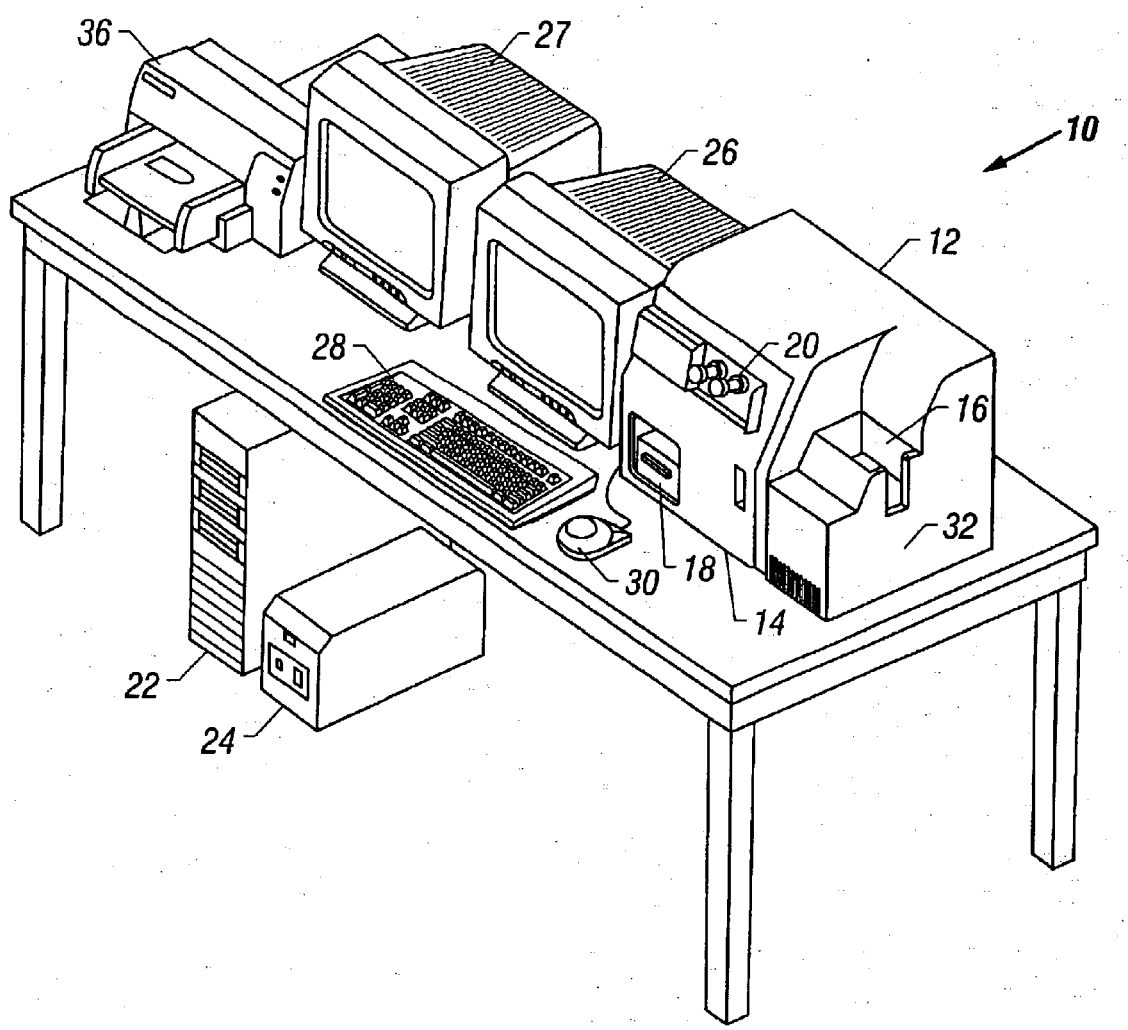
FIG. 1 is a perspective view of an apparatus for automated cell analysis embodying the present invention.
Figure 2:
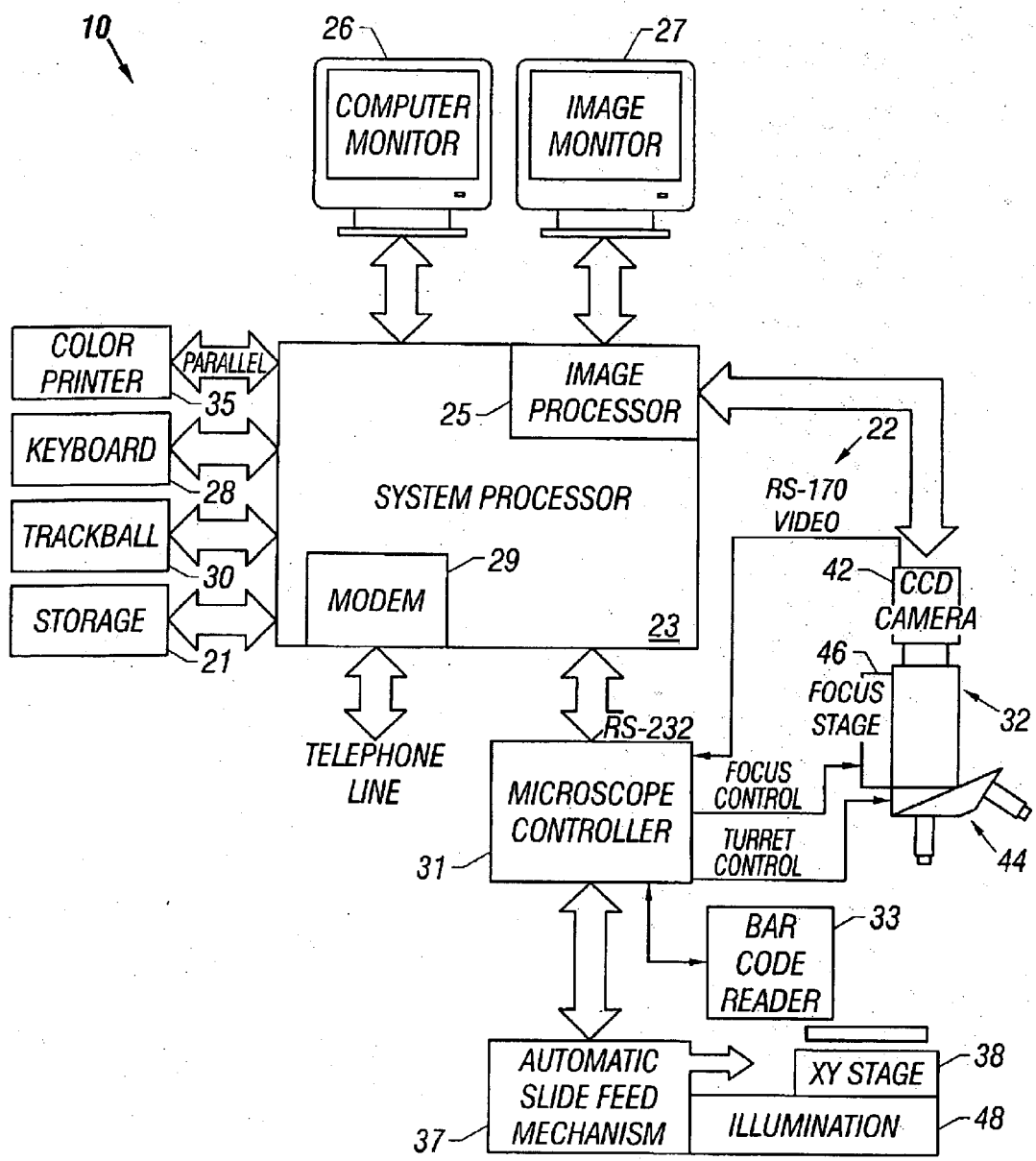
FIG. 2 is a block diagram of the apparatus shown in FIG. 1.

Referring now to the figures, an apparatus for automated cell analysis of biological specimens is generally indicated by reference numeral 10 as shown in perspective view in FIG. 1 and in block diagram form in FIG. 2. The apparatus 10 comprises a microscope subsystem 32 housed in a housing 12. The housing 12 includes a slide carrier input hopper 16 and a slide carrier output hopper 18. A door 14 in the housing 12 secures the microscope subsystem from the external environment. A computer subsystem comprises a computer 22 having a system processor 23, an image processor 25 and a communications modem 29. The computer subsystem further includes a computer monitor 26 and an image monitor 27 and other external peripherals including storage device 21, track ball device 30, keyboard 28 and color printer 35. An external power supply 24 is also shown for powering the system. Viewing oculars 20 of the microscope subsystem project from the housing 12 for operator viewing. The apparatus 10 further includes a CCD camera 42 for acquiring images through the microscope subsystem 32. A microscope controller 31 under the control of system processor 23 controls a number of microscope subsystem functions described further in detail. An automatic slide feed mechanism 37 in conjunction with X-Y stage 38 provide automatic slide handling in the apparatus 10. An illumination light source 48 projects light onto the X-Y stage 38 which is subsequently imaged through the microscope subsystem 32 and acquired through CCD camera 42 for processing in the image processor 25. A Z stage or focus stage 46 under control of the microscope controller 31 provides displacement of the microscope subsystem in the Z plane for focusing. The microscope subsystem 32 further includes a motorized objective turret 44 for selection of objectives.

The purpose of the apparatus 10 is for the unattended automatic scanning of prepared microscope slides for the detection and counting of candidate objects of interest such as normal and abnormal cells, e.g., tumor cells. The preferred embodiment may be utilized for rare event detection in which there may be only one candidate object of interest per several hundred thousand normal cells, e.g., one to five candidate objects of interest per 2 square centimeter area of the slide. The apparatus 10 automatically locates and counts candidate objects of interest and estimates normal cells present in a biological specimen on the basis of color, size and shape characteristics. A number of stains are used to preferentially stain candidate objects of interest and normal cells different colors so that such cells can be distinguished from each other.

As noted in the background of the invention, a biological specimen may be prepared with a reagent to obtain a colored insoluble precipitate. The apparatus of the present invention is used to detect this precipitate as a candidate object of interest.

Figure 8:
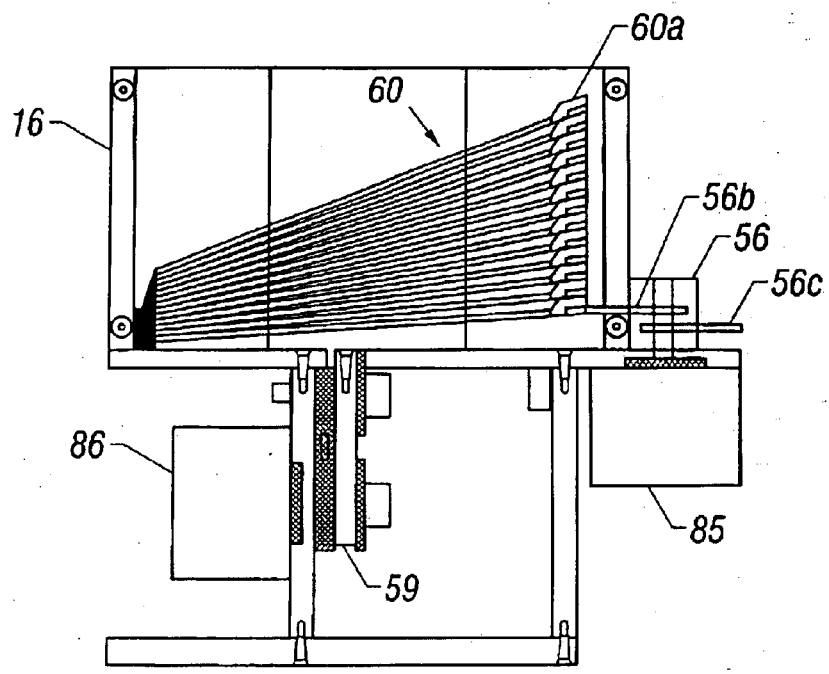
FIG. 8 is an end view of the input module of the automated slide handling subsystem.
Figure 8A:
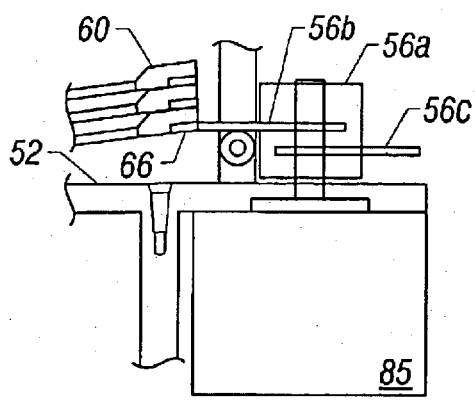
FIGS. 8a–8d illustrate the input operation of the automatic slide handling subsystem.
Figure 8B:
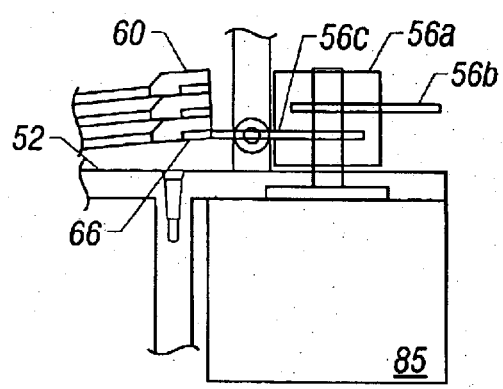

During operation of the apparatus 10, a pathologist or laboratory technician mounts prepared slides onto slide carriers. A slide carrier 60 is illustrated in FIG. 8 and will be described further below. Each slide carrier holds up to 4 slides. Up to 25 slide carriers are then loaded into input hopper 16. The operator can specify the size, shape and location of the area to be scanned or alternatively, the system can automatically locate this area. The operator then commands the system to begin automated scanning of the slides through a graphical user interface. Unattended scanning begins with the automatic loading of the first carrier and slide onto the precision motorized X-Y stage 38. A bar code label affixed to the slide is read by a bar code reader 33 during this loading operation. Each slide is then scanned at a user selected low microscope magnification, for example, 10×, to identify candidate cells based on their color, size and shape characteristics. The X-Y locations of candidate cells are stored until scanning is completed.

After the low magnification scanning is completed, the apparatus automatically returns to each candidate cell, reimages and refocuses at a higher magnification such as 40× and performs further analysis to confirm the cell candidate. The apparatus stores an image of the cell for later review by a pathologist. All results and images can be stored to a storage device 21 such as a removable hard drive or DAT tape or transmitted to a remote site for review or storage. The stored images for each slide can be viewed in a mosaic of images for further review. In addition, the pathologist or operator can also directly view a detected cell through the microscope using the included oculars 20 or on image monitor 27.

Figure 3:
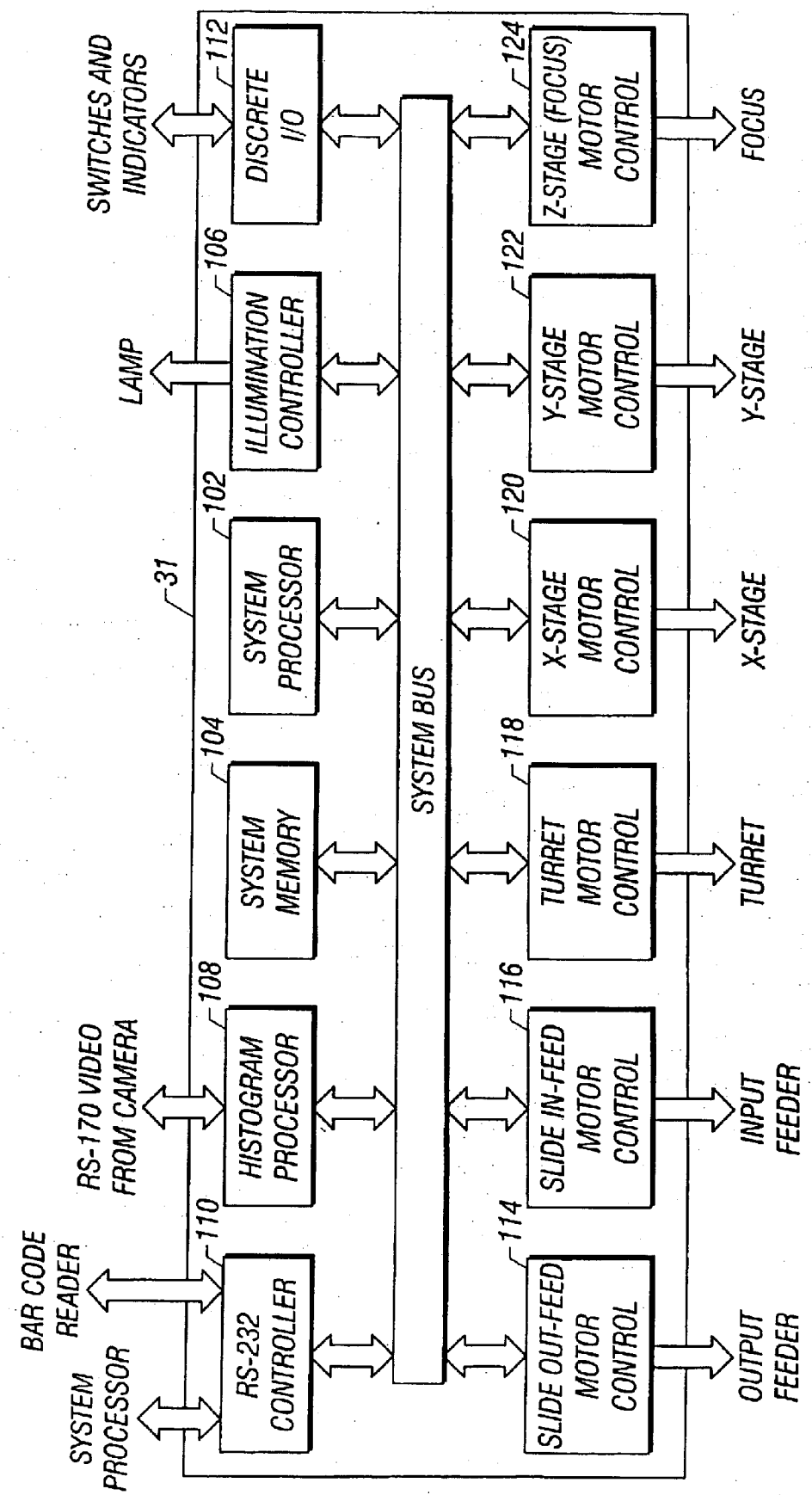
FIG. 3 is a block diagram of the microscope controller of FIG. 2.

Having described the overall operation of the apparatus 10 from a high level, the further details of the apparatus will now be described. Referring to FIG. 3, the microscope controller 31 is shown in more detail. The microscope controller 31 includes a number of subsystems connected through a system bus. A system processor 102 controls these subsystems and is controlled by the apparatus system processor 23 through an RS 232 controller 110. The system processor 102 controls a set of motor—control subsystems 114 through 124 which control the input and output feeder, the motorized turret 44, the X-Y stage 38, and the Z stage 46 (FIG. 2). A histogram processor 108 receives input from CCD camera 42 for computing variance data during the focusing operation described further herein.

The system processor 102 further controls an illumination controller 106 for control of substage illumination 48. The light output from the halogen light bulb which supplies illumination for the system can vary over time due to bulb aging, changes in optical alignment, and other factors. In addition, slides which have been "over stained" can reduce the camera exposure to an unacceptable level. In order to compensate for these effects, the illumination controller 106 is included. This controller is used in conjunction with light control software to compensate for the variations in light level. The light control software samples the output from the camera at intervals (such as between loading of slide carriers), and commands the controller to adjust the light level to the desired levels. In this way, light control is automatic and transparent to the user and adds no additional time to system operation.

The system processor 23 is preferably comprised of dual parallel Intel Pentium 90 MHz devices. The image processor 25 is preferably a Matrox Imaging Series 640 model. The microscope controller system processor 102 is an Advanced Micro Devices AMD29K device.

Figure 4:
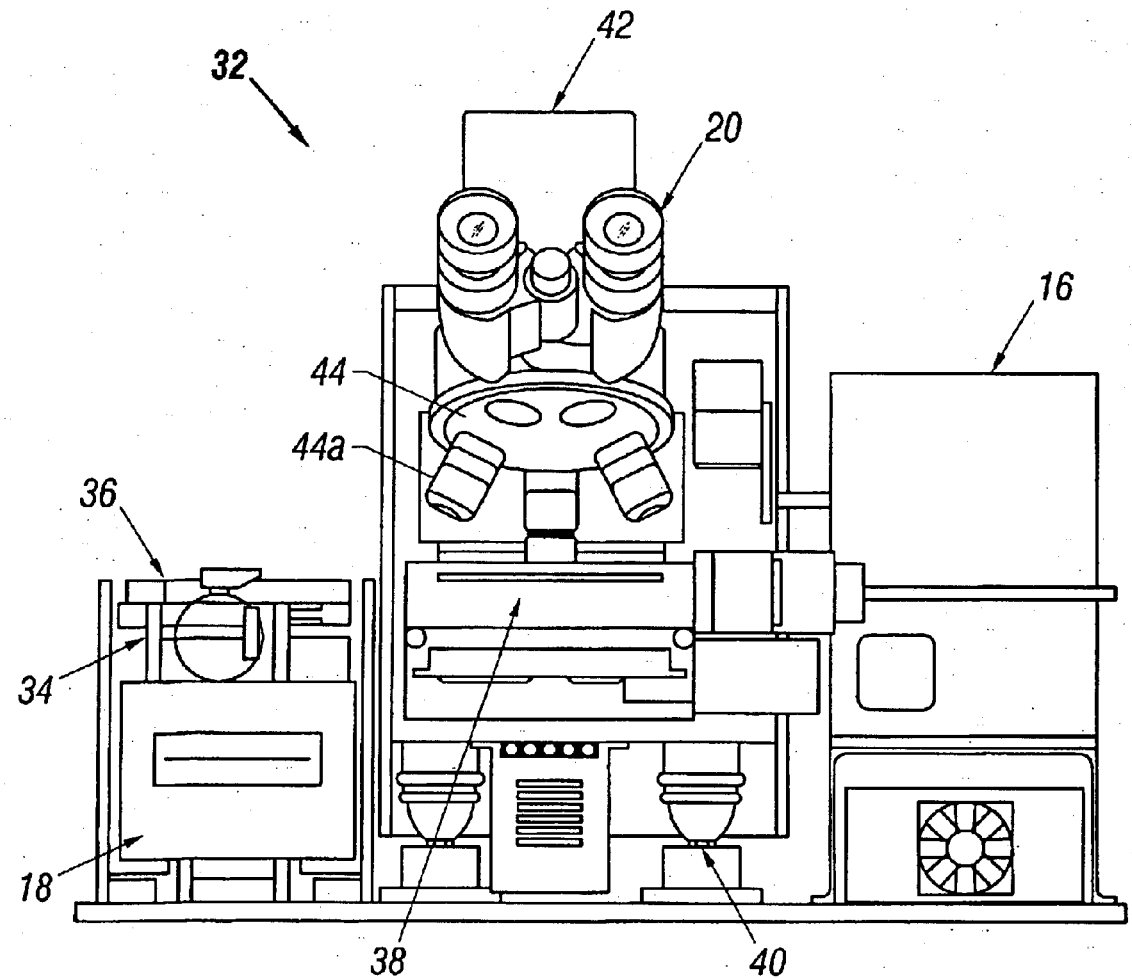
FIG. 4 is a plan view of the apparatus of FIG. 1 having the housing removed.
Figure 5:
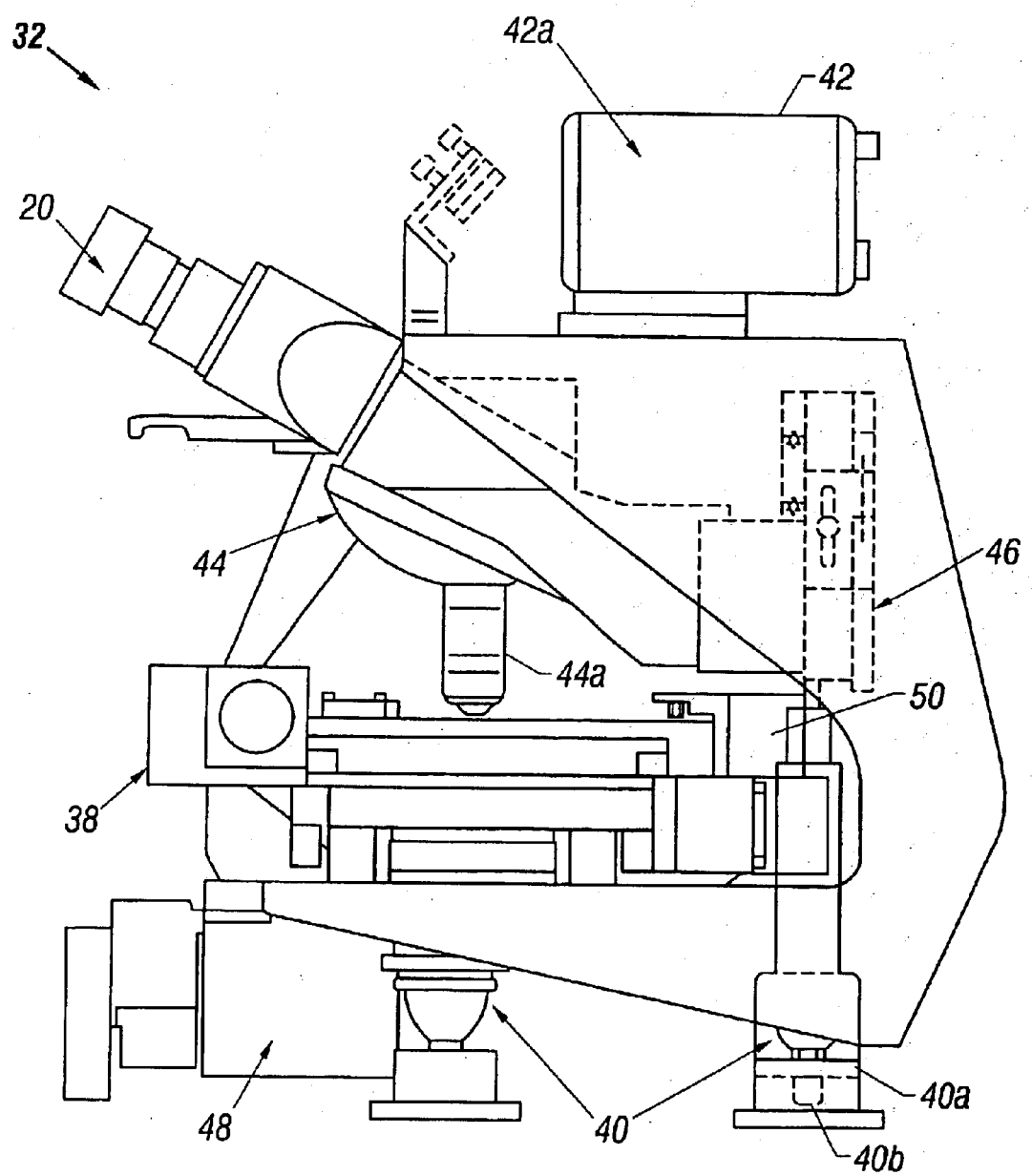
FIG. 5 is a side view of a microscope subsystem of the apparatus of FIG. 1.

Referring now to FIGS. 4 and 5, further detail of the apparatus 10 is shown. FIG. 4 shows a plan view of the apparatus 10 with the housing 12 removed. A portion of the automatic slide feed mechanism 37 is shown to the left of the microscope subsystem 32 and includes slide carrier unloading assembly 34 and unloading platform 36 which in conjunction with slide carrier output hopper 18 function to receive slide carriers which have been analyzed.

Vibration isolation mounts 40, shown in further detail in FIG. 5, are provided to isolate the microscope subsystem 32 from mechanical shock and vibration that can occur in a typical laboratory environment. In addition to external sources of vibration, the high speed operation of the X-Y stage 38 can induce vibration into the microscope subsystem 32. Such sources of vibration can be isolated from the electro-optical subsystems to avoid any undesirable effects on image quality. The isolation mounts 40 comprise a spring 40*a* and piston 40*b* submerged in a high viscosity silicon gel which is enclosed in an elastomer membrane bonded to a casing to achieve damping factors on the order of 17 to 20%.

Figure 6A:
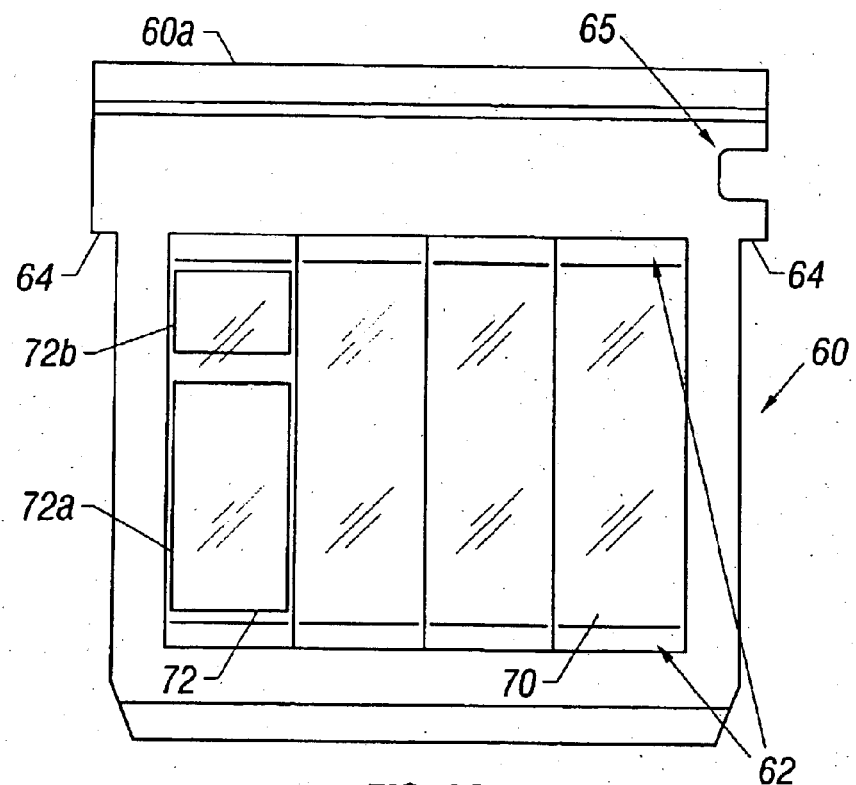
FIG. 6a is a top view of a slide carrier for use with the apparatus of FIG. 1.
Figure 6B:
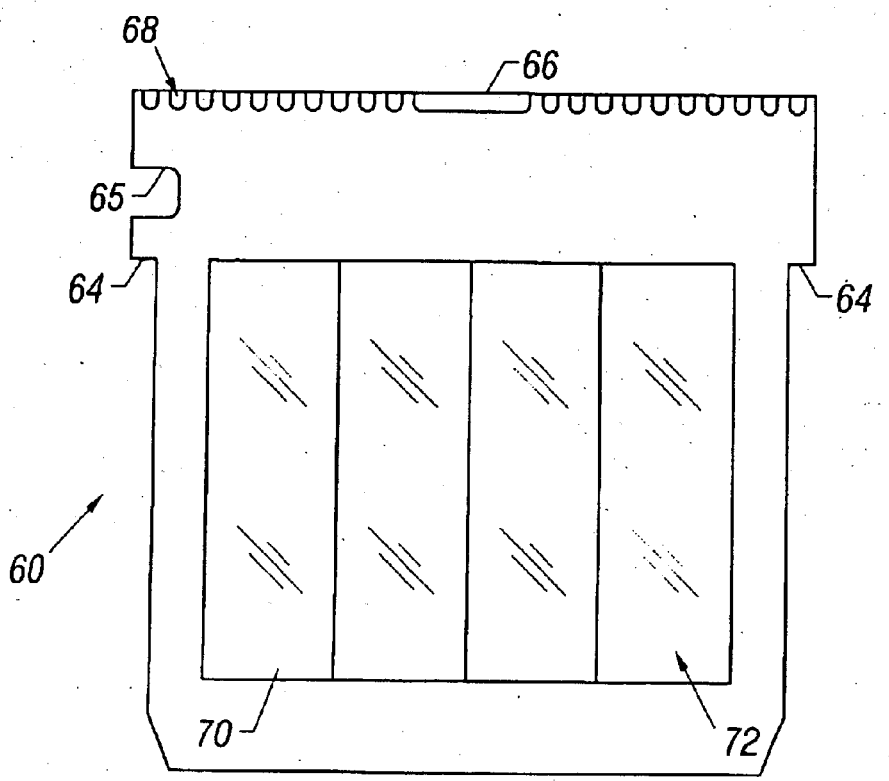

The automatic slide handling feature of the present invention will now be described. The automated slide handling subsystem operates on a single slide carrier at a time. A slide carrier 60 is shown in FIGS. 6*a* and 6*b* which provide a top view and a bottom view respectively. The slide carrier 60 includes up to four slides 70 mounted with adhesive tape 62. The carrier 60 includes ears 64 for hanging the carrier in the output hopper 18. An undercut 66 and pitch rack 68 are formed at the top edge of the slide carrier 60 for mechanical handling of the slide carrier. A keyway cutout 65 is formed in one side of the carrier 60 to facilitate carrier alignment. A prepared slide 72 mounted on the slide carrier 60 includes a sample area 72*a* and a bar code label area 72*b*.

Figure 7A:
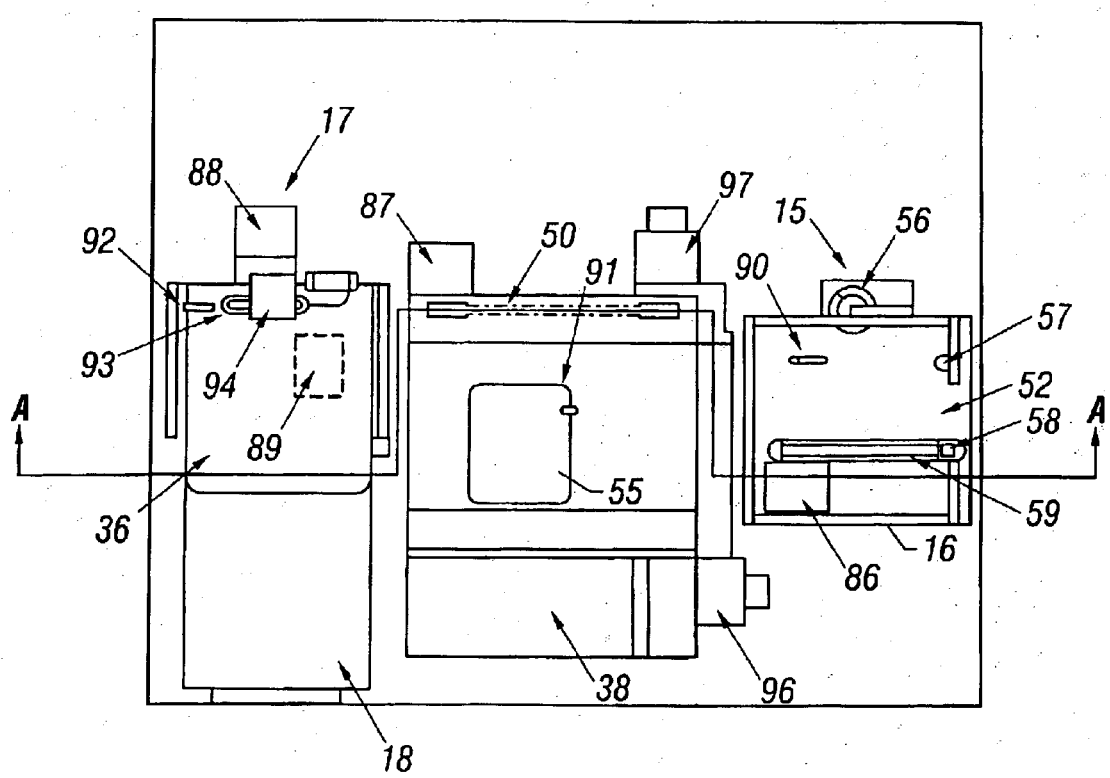
FIG. 7a is a top view of an automated slide handling subsystem of the apparatus of FIG. 1.
Figure 7B:
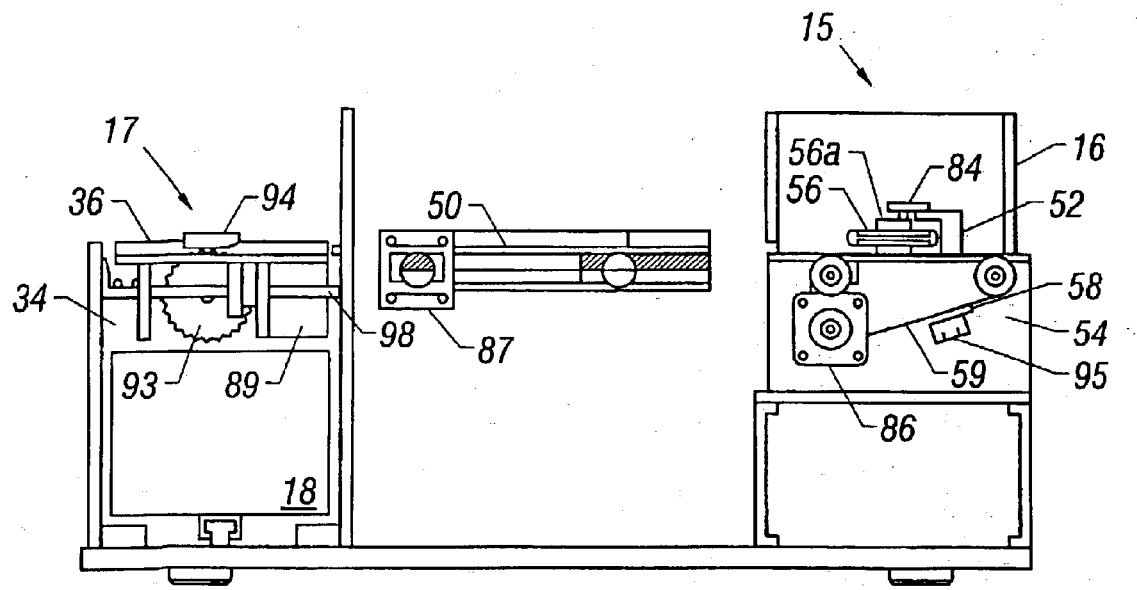
FIG. 7b is a partial cross-sectional view of the automated slide handling subsystem of FIG. 7a taken on line A—A.

FIG. 7*a* provides a top view of the slide handling subsystem which comprises a slide input module 15, a slide output module 17 and X-Y stage drive belt 50. FIG. 7*b* provides a partial cross-sectional view taken along line A—A of FIG. 7*a*.

The slide input module 15 comprises a slide carrier input hopper 16, loading platform 52 and slide carrier loading subassembly 54. The input hopper 16 receives a series of slide carriers 60 (FIGS. 6*a* and 6*b*) in a stack on loading platform 52. A guide key 57 protrudes from a side of the input hopper 16 to which the keyway cutout 65 (FIG. 6*a*) of the carrier is fit to achieve proper alignment.

The input module 15 further includes a revolving indexing cam 56 and a switch 90 mounted in the loading platform 52, the operation of which is described further below. The carrier loading subassembly 54 comprises an infeed drive belt 59 driven by a motor 86. The infeed drive belt 59 includes a pusher tab 58 for pushing the slide carrier horizontally toward the X-Y stage 38 when the belt is driven. A homing switch 95 senses the pusher tab 58 during a revolution of the belt 59.

Referring specifically to FIG. 7*a*, the X-Y stage 38 is shown with x position and y position motors 96 and 97 respectively which are controlled by the microscope controller 31 (FIG. 3) and are not considered part of the slide handling subsystem. The X-Y stage 38 further includes an aperture 55 for allowing illumination to reach the slide carrier. A switch 91 is mounted adjacent the aperture 55 for sensing contact with the carrier and thereupon activating a motor 87 to drive stage drive belt 50 (FIG. 7*b*). The drive belt 50 is a double sided timing belt having teeth for engaging pitch rack 68 of the carrier 60 (FIG. 6*b*).

The slide output module 17 includes slide carrier output hopper 18, unloading platform 36 and slide carrier unloading subassembly 34. The unloading subassembly 34 comprises a motor 89 for rotating the unloading platform 36 about shaft 98 during an unloading operation described further below. An outfeed gear 93 driven by motor 88 rotatably engages the pitch rack 68 of the carrier 60 (FIG. 6*b*) to transport the carrier to a rest position against switch 92. A springloaded hold-down mechanism holds the carrier in place on the unloading platform 36.

The slide handling operation will now be described. Referring to FIG. 8, a series of slide carriers 60 are shown stacked in input hopper 16 with the top edges 60*a* aligned. As the slide handling operation begins, the indexing cam 56 driven by motor 85 advances one revolution to allow only one slide carrier to drop to the bottom of the hopper 16 and onto the loading platform 52.

Figure 8C:
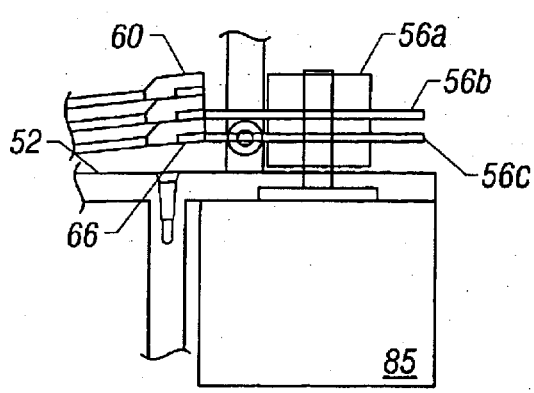
Figure 8D:
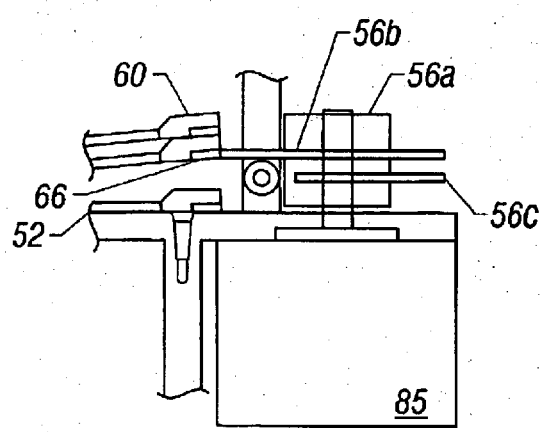

FIGS. 8*a*–8*d* show the cam action in more detail. The cam 56 includes a hub 56*a* to which are mounted upper and lower leaves 56*b* and 56*c* respectively. The leaves 56*b*, 56*c* are semicircular projections oppositely positioned and spaced apart vertically. In a first position shown in FIG. 8*a*, the upper leaf 56*b* supports the bottom carrier at the undercut portion 66. At a position of the cam 56 rotated 180°, shown in FIG. 8*b*, the upper leaf 56*b* no longer supports the carrier and instead the carrier has dropped slightly and is supported by the lower leaf 56*c*. FIG. 8*c* shows the position of the cam 56 rotated 270° wherein the upper leaf 56*b* has rotated sufficiently to begin to engage the undercut 66 of the next slide carrier while the opposite facing lower leaf 56*c* still supports the bottom carrier. After a full rotation of 360° as shown in FIG. 8*d*, the lower leaf 56*c* has rotated opposite the carrier stack and no longer supports the bottom carrier which now rests on the loading platform 52. At the same position, the upper leaf 56*b* supports the next carrier for repeating the cycle.

Referring again to FIGS. 7*a* and 7*b*, when the carrier drops to the loading platform 52, the contact closes switch 90 which activates motors 86 and 87. Motor 86 drives the infeed drive belt 59 until the pusher tab 58 makes contact with the carrier and pushes the carrier onto the X-Y stage drive belt 50. The stage drive belt 50 advances the carrier until contact is made with switch 91, the closing of which begins the slide scanning process described further herein. Upon completion of the scanning process, the X-Y stage 38 moves to an unload position and motors 87 and 88 are activated to transport the carrier to the unloading platform 36 using stage drive belt 50. As noted, motor 88 drives outfeed gear 93 to engage the carrier pitch rack 68 of the carrier 60 (FIG. 6*b*) until switch 92 is contacted. Closing switch 92 activates motor 89 to rotate the unloading platform 36.

Figure 9A:
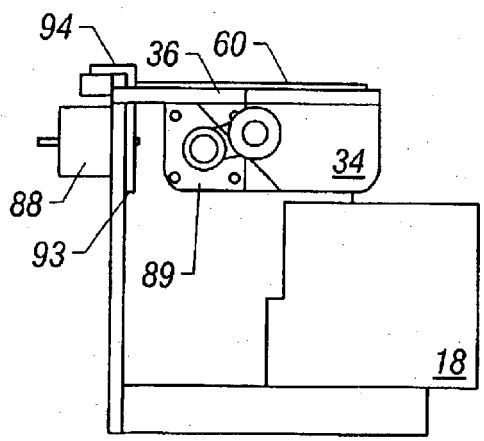
FIGS. 9a–9d illustrate the output operation of the automated slide handling subsystem.
Figure 9B:
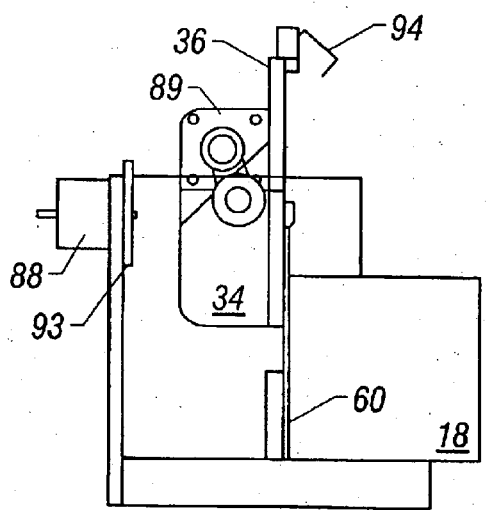
Figure 9C:
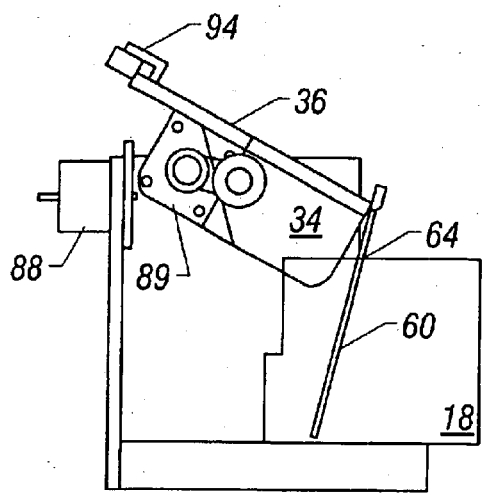
Figure 9D:
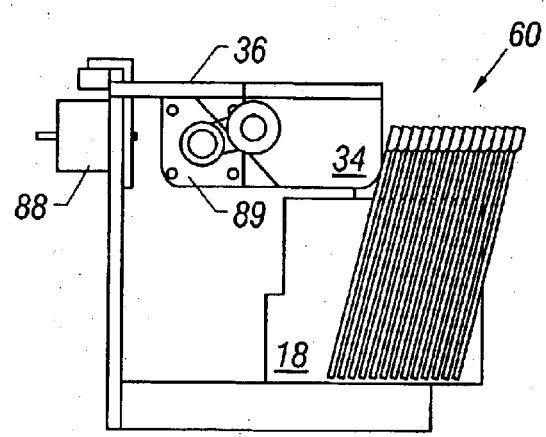

The unloading operation is shown in more detail in end views of the output module 17 (FIGS. 9*a*–9*d*). In FIG. 9*a*, the unloading platform 36 is shown in a horizontal position supporting a slide carrier 60. The hold-down mechanism 94 secures the carrier 60 at one end. FIG. 9*b* shows the output module 17 after motor 89 has rotated the unloading platform 36 to a vertical position, at which point the spring loaded hold-down mechanism 94 releases the slide carrier 60 into the output hopper 18. The carrier 60 is supported in the output hopper 18 by means of ears 64 (FIGS. 6*a* and 6*b*). FIG. 9*c* shows the unloading platform 36 being rotated back towards the horizontal position. As the platform 36 rotates upward, it contacts the deposited carrier 60 and the upward movement pushes the carrier toward the front of the output hopper 18. FIG. 9*d* shows the unloading platform 36 at its original horizontal position after having output a series of slide carriers 60 to the output hopper 18.

Having described the overall system and the automated slide handling feature, the aspects of the apparatus 10 relating to scanning, focusing and image processing will now be described in further detail.

In some cases, an operator will know ahead of time where the scan area of interest is on the slide. Conventional preparation of slides for examination provides repeatable and known placement of the sample on the slide. The operator can therefore instruct the system to always scan the same area at the same location of every slide which is prepared in this fashion. But there are other times in which the area of interest is not known, for example, where slides are prepared manually with a known smear technique. One feature of the invention automatically determines the scan area using a texture analysis process.

Figure 10:
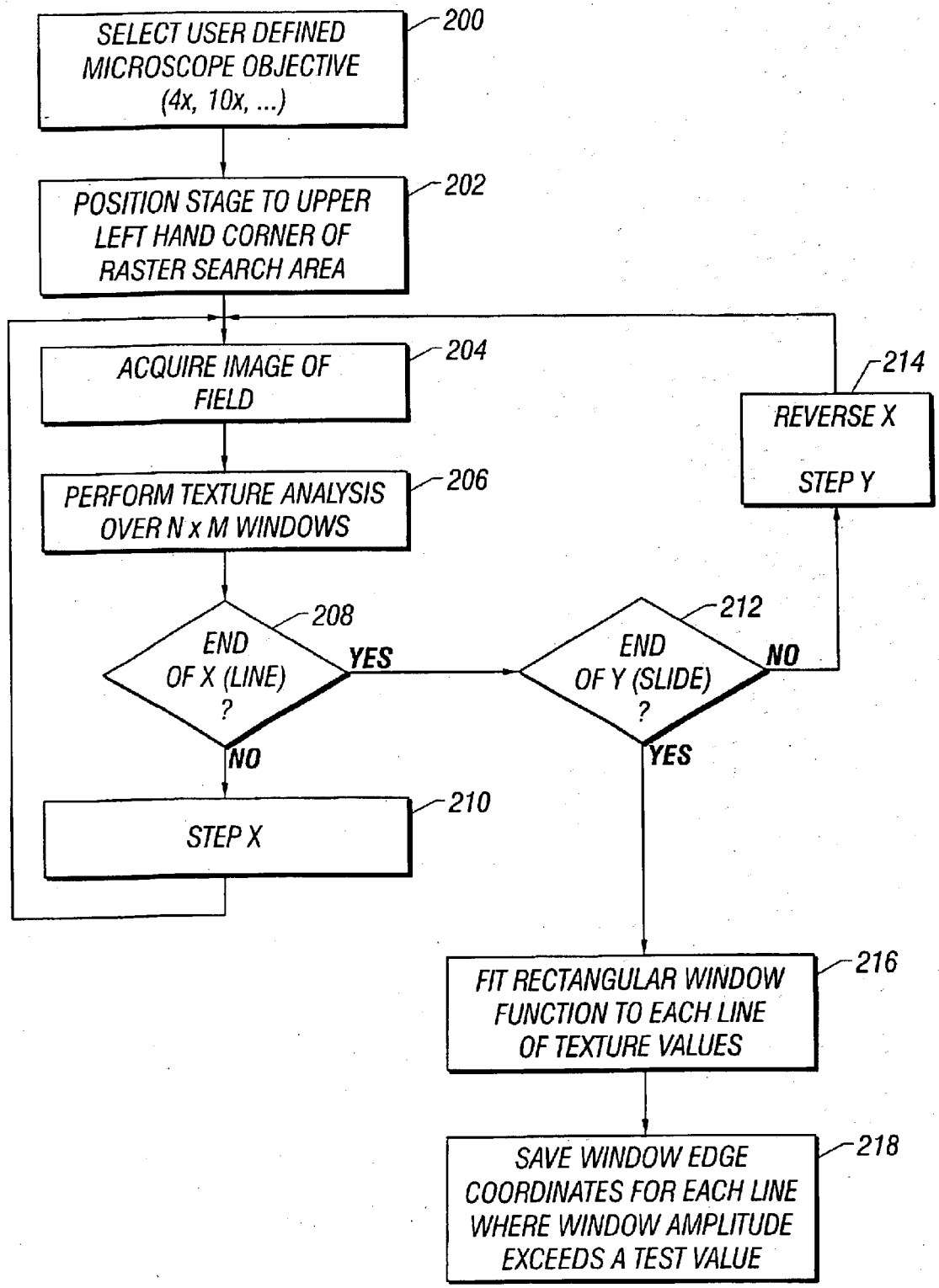
FIG. 10 is a flow diagram of the procedure for automatically determining a scan area.

FIG. 10 is a flow diagram that describes the processing associated with the automatic location of a scan area. As shown in this figure, the basic method is to pre-scan the entire slide area to determine texture features that indicate the presence of a smear and to discriminate these areas from dirt and other artifacts.

Figure 12:
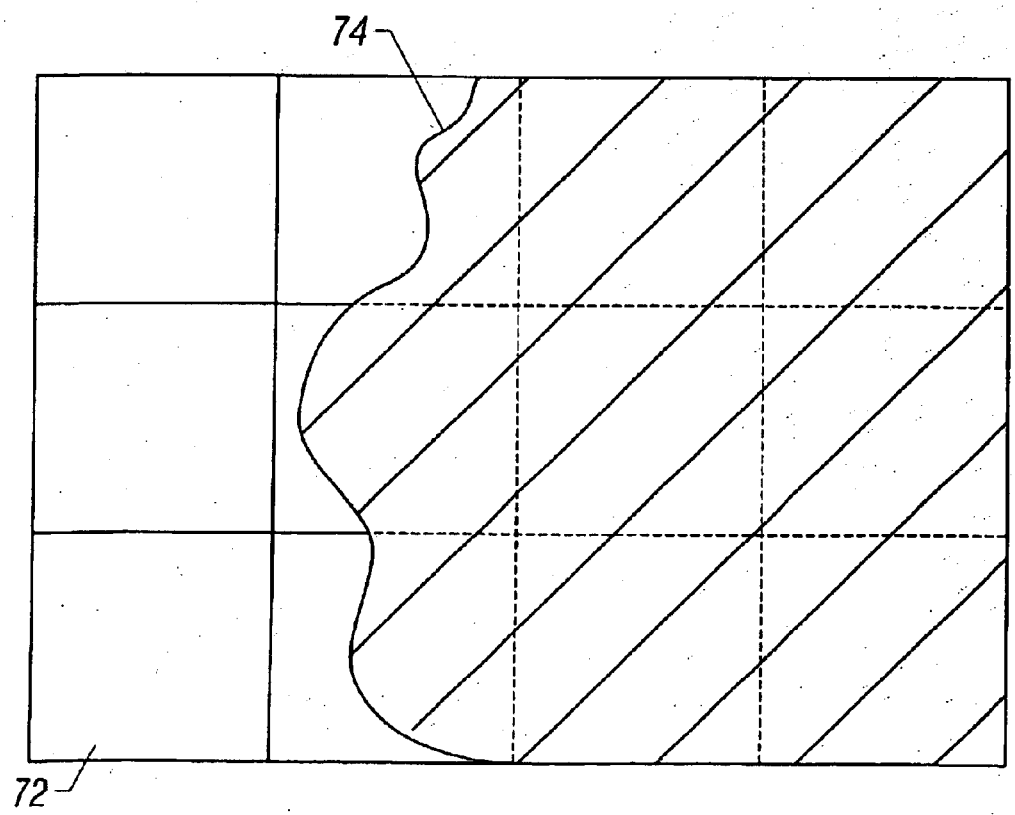
FIG. 12 illustrates an image of a field acquired in the procedure of FIG. 10.

At each location of this raster scan, an image such as in FIG. 12 is acquired and analyzed for texture information at steps 204 and 206. Since it is desired to locate the edges of the smear sample within a given image, texture analyses are conducted over areas called windows 78, which are smaller than the entire image as shown in FIG. 12. The process iterates the scan across the slide at steps 208, 210, 212 and 214.

Figure 11:
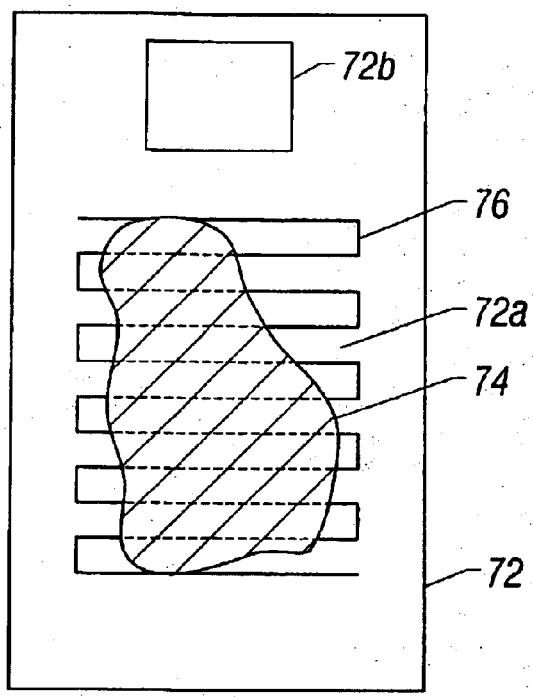
FIG. 11 shows the scan path on a prepared slide in the procedure of FIG. 10.

In the interest of speed, the texture analysis process is performed at a lower magnification, preferably at a 4× objective. One reason to operate at low magnification is to image the largest slide area at any one time. Since cells do not yet need to be resolved at this stage of the overall image analysis, the 4× magnification is preferred. On a typical slide, as shown in FIG. 11, a portion 72b of the end of the slide 72 is reserved for labeling with identification information. Excepting this label area, the entire slide is scanned in a raster scan fashion 76 to yield a number of adjacent images.

Texture values for each window include the pixel variance over a window, the difference between the largest and smallest pixel value within a window, and other indicators. The presence of a smear raises the texture values compared with a blank area.

One problem with a smear from the standpoint of determining its location is its non-uniform thickness and texture. For example, the smear is likely to be relatively thin at the edges and thicker towards the middle due to the nature of the smearing process. To accommodate for the non-uniformity, texture analysis provides a texture value for each analyzed area. The texture value tends to gradually rise as the scan proceeds across a smear from a thin area to a thick area, reaches a peak, and then falls off again to a lower value as a thin area at the edge is reached. The problem is then to decide from the series of texture values the beginning and ending, or the edges, of the smear. The texture values are fit to a square wave waveform since the texture data does not have sharp beginnings and endings.

After conducting this scanning and texture evaluation operation, one must determine which areas of elevated texture values represent the desired smear 74, and which represent undesired artifacts. This is accomplished by fitting a step function, on a line by line basis to the texture values in step 216. This function, which resembles a single square wave across the smear with a beginning at one edge, and end at the other edge, and an amplitude provides the means for discrimination. The amplitude of the best-fit step function is utilized to determine whether smear or dirt is present since relatively high values indicate smear. If it is decided that smear is present, the beginning and ending coordinates of this pattern are noted until all lines have been processed, and the smear sample area defined at 218.

After an initial focusing operation described further herein, the scan area of interest is scanned to acquire images for image analysis. The preferred method of operation is to initially perform a complete scan of the slide at low magnification to identify and locate candidate objects of interest, followed by further image analysis of the candidate objects of interest at high magnification in order to confirm the objects as cells. An alternate method of operation is to perform high magnification image analysis of each candidate object of interest immediately after the object has been identified at low magnification. The low magnification scanning then resumes, searching for additional candidate objects of interest. Since it takes on the order of a few seconds to change objectives, this alternate method of operation would take longer to complete.

The operator can pre-select a magnification level to be used for the scanning operation. A low magnification using a 10× objective is preferred for the scanning operation since a larger area can be initially analyzed for each acquired scan image. The overall detection process for a cell includes a combination of decisions made at both low (10×) and high magnification (40×) levels. Decision making at the 10× magnification level is broader in scope, i.e., objects that loosely fit the relevant color, size and shape characteristics are identified at the 10× level. Analysis at the 40× magnification level then proceeds to refine the decision making and confirm objects as likely cells or candidate objects of interest. For example, at the 40× level it is not uncommon to find that some objects that were identified at 10× are artifacts which the analysis process will then reject. In addition, closely packed objects of interest appearing at 10× are separated at the 40× level.

In a situation where a cell straddles or overlaps adjacent image fields, image analysis of the individual adjacent image fields could result in the cell being rejected or undetected. To avoid missing such cells, the scanning operation compensates by overlapping adjacent image fields in both the x and y directions. An overlap amount greater than half the diameter of an average cell is preferred. In the preferred embodiment, the overlap is specified as a percentage of the image field in the x and y directions.

The time to complete an image analysis can vary depending upon the size of the scan area and the number of candidate cells, or objects of interest identified. For one example, in the preferred embodiment, a complete image analysis of a scan area of two square centimeters in which 50 objects of interest are confirmed can be performed in about 12 to 15 minutes. This example includes not only focusing, scanning and image analysis but also the saving of 40× images as a mosaic on hard drive 21 (FIG. 2).

Consider the utility of the present invention in a "rare event" application where there may be one, two or a very small number of cells of interest located somewhere on the slide. To illustrate the nature of the problem by analogy, if one were to scale a slide to the size of a football field, a tumor cell, for example, would be about the size of a bottle cap. The problem is then to rapidly search the football field and find the very small number of bottle caps and have a high certainty that none have been missed.

However the scan area is defined, an initial focusing operation must be performed on each slide prior to scanning. This is required since slides differ, in general, in their placement in a carrier. These differences include slight (but significant) variations of tilt of the slide in its carrier. Since each slide must remain in focus during scanning, the degree of tilt of each slide must be determined. This is accomplished with an initial focusing operation that determines the exact degree of tilt, so that focus can be maintained automatically during scanning.

The initial focusing operation and other focusing operations to be described later utilize a focusing method based on processing of images acquired by the system. This method was chosen for its simplicity over other methods including use of IR beams reflected from the slide surface and use of mechanical gauges. These other methods also would not function properly when the specimen is protected with a coverglass. The preferred method results in lower system cost and improved reliability since no additional parts need be included to perform focusing.

Figure 13A:
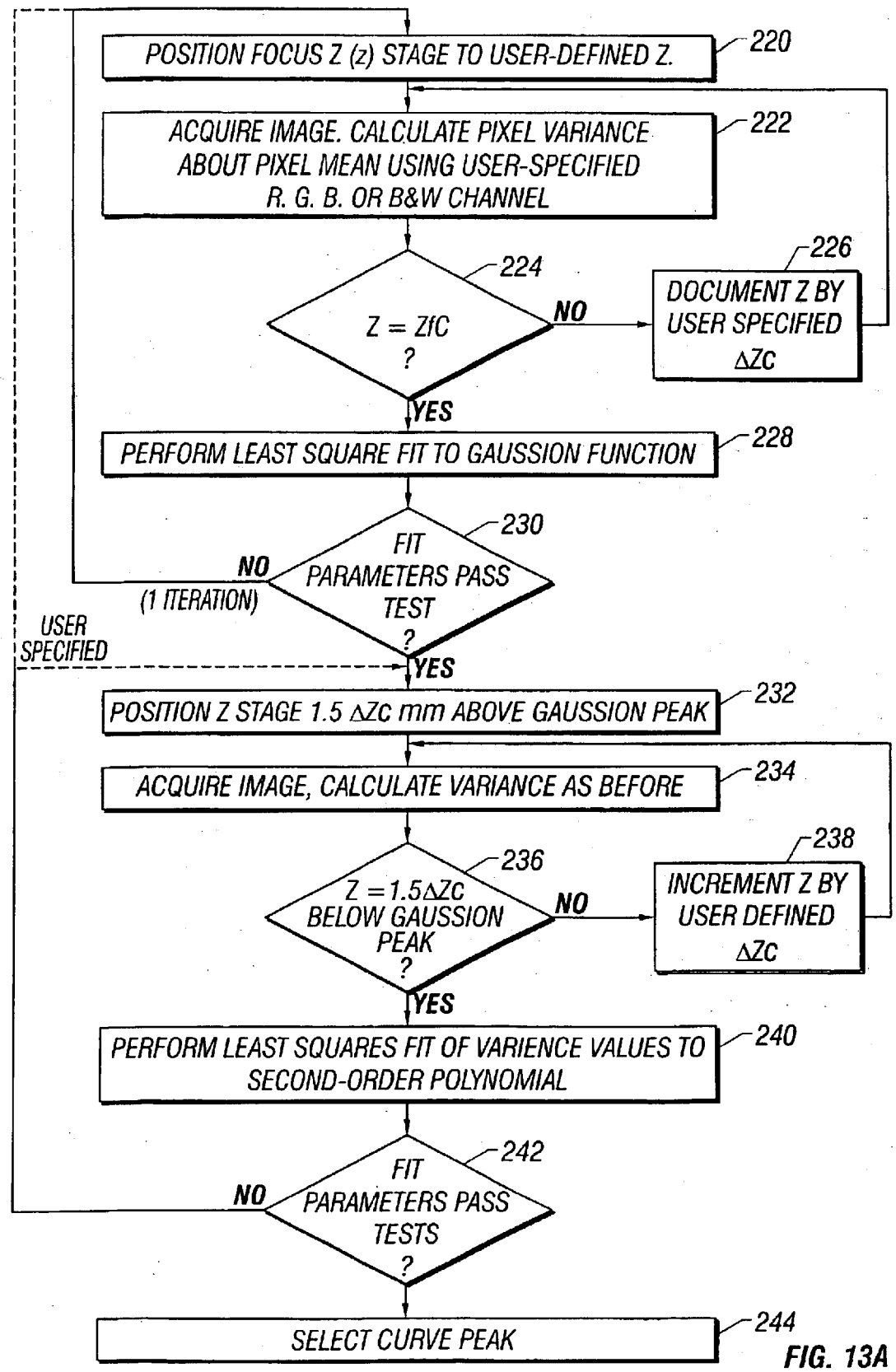
FIG. 13A is a flow diagram of a preferred procedure for determining a focal position.

FIG. 13A provides a flow diagram describing the "focus point" procedure. The basic method relies on the fact that the pixel value variance (or standard deviation) taken about the pixel value mean is maximum at best focus. A "brute-force" method could simply step through focus, using the computer controlled Z, or focus stage, calculate the pixel variance at each step, and return to the focus position providing the maximum variance. Such a method would be too time consuming. Therefore, additional features were added as shown in FIG. 13A.

These features include the determination of pixel variance at a relatively coarse number of focal positions, and then the fitting of a curve to the data to provide a faster means of determining optimal focus. This basic process is applied in two steps, coarse and fine.

During the coarse step at 220–230, the Z stage is stepped over a user-specified range of focus positions, with step sizes that are also user-specified. It has been found that for coarse focusing, these data are a close fit to a Gaussian function. Therefore, this initial set of variance versus focus position data are least-squares fit to a Gaussian function at 228. The location of the peak of this Gaussian curve determines the initial or coarse estimate of focus position for input to step 232.

Following this, a second stepping operation 232–242 is performed utilizing smaller steps over a smaller focus range centered on the coarse focus position. Experience indicates that data taken over this smaller range are generally best fit by a second order polynomial. Once this least squares fit is performed at 240, the peak of the second order curve provides the fine focus position at 244.

Figure 14:
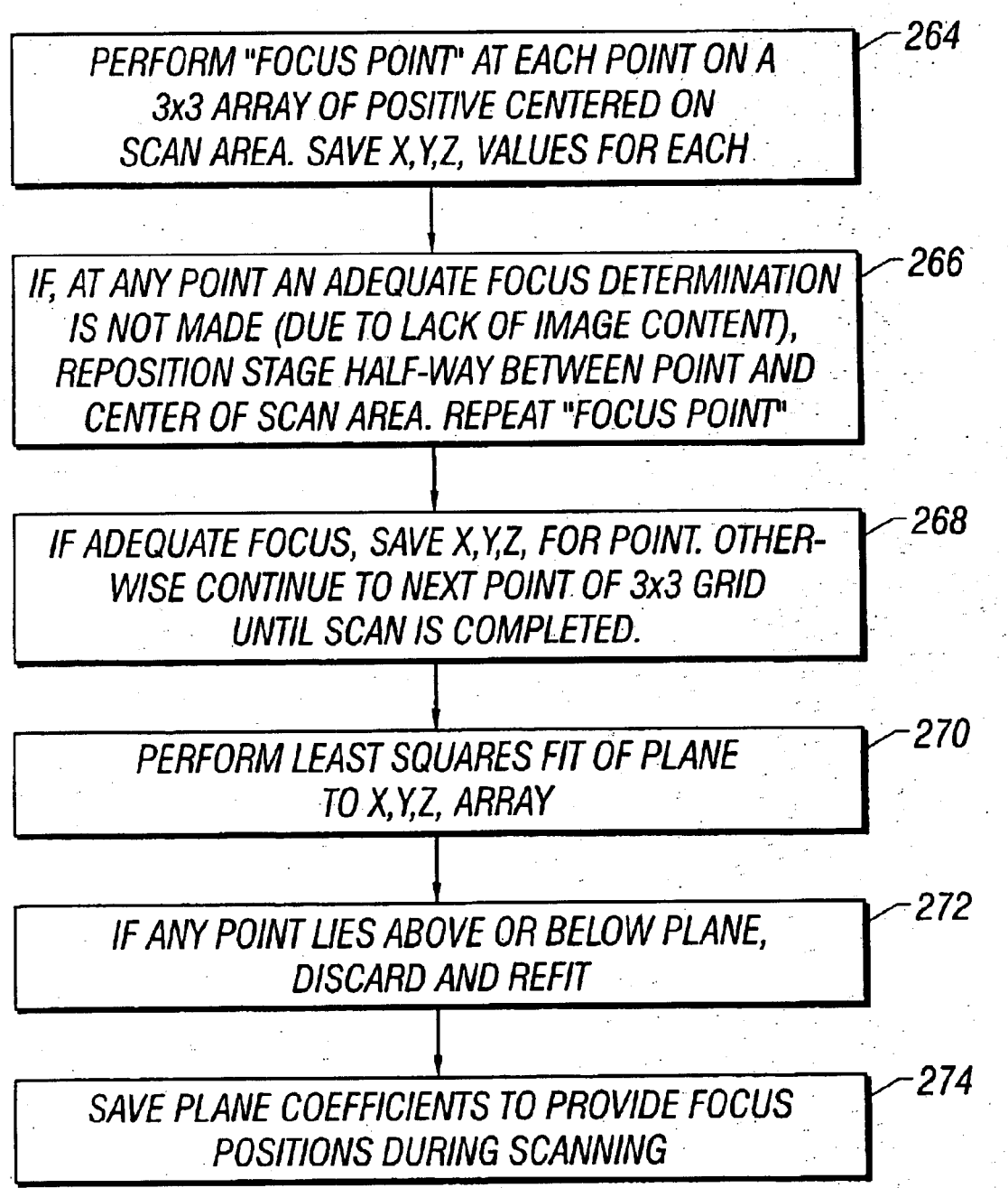
FIG. 14 is a flow diagram of a procedure for automatically determining initial focus.
Figure 15:
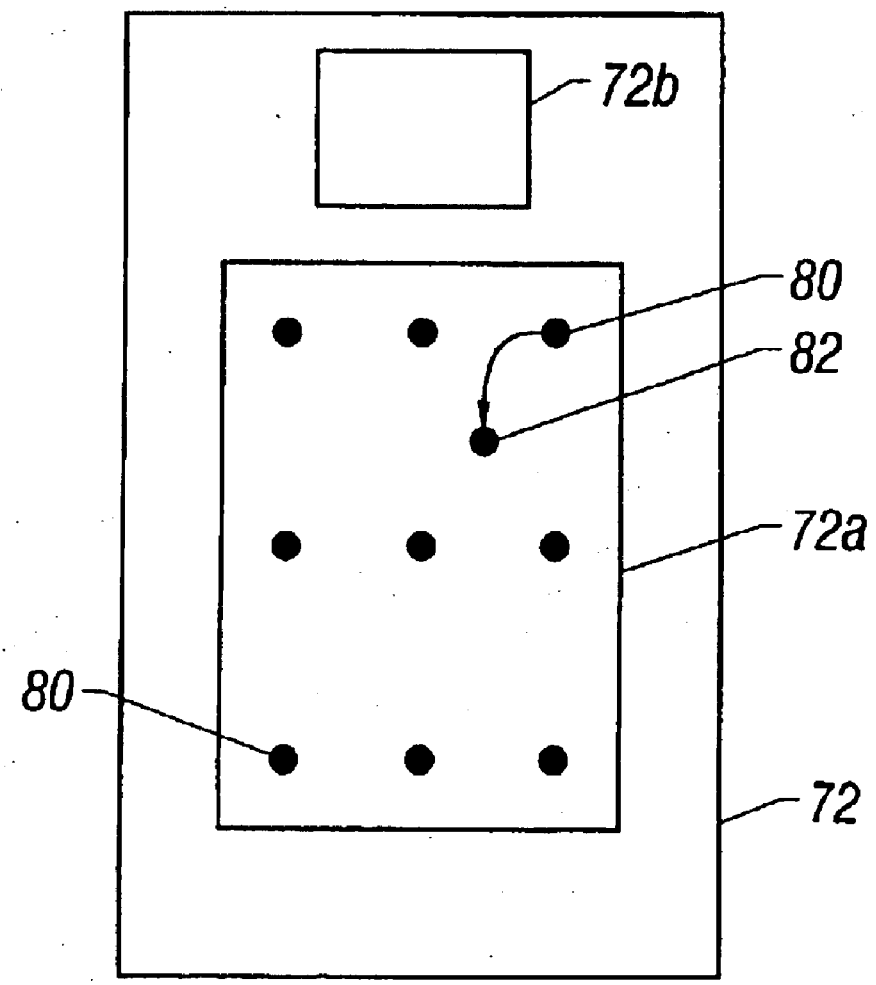
FIG. 15 shows an array of slide positions for use in the procedure of FIG. 14.

FIG. 14 illustrates a procedure for how this focusing method is utilized to determine the orientation of a slide in its carrier. As shown, focus positions are determined, as described above, for a 3×3 grid of points centered on the scan area at 264. Should one or more of these points lie outside the scan area, the method senses at 266 this by virtue of low values of pixel variance. In this case, additional points are selected closer to the center of the scan area. FIG. 15 shows the initial array of points 80 and new point 82 selected closer to the center. Once this array of focus positions is determined at 268, a least squares plane is fit to this data at 270. Focus points lying too far above or below this best-fit plane are discarded at 272 (such as can occur from a dirty cover glass over the scan area), and the data is then refit. This plane at 274 then provides the desired Z position information for maintaining focus during scanning.

After determination of the best-fit focus plane, the scan area is scanned in an X raster scan over the scan area as described earlier. During scanning, the X stage is positioned to the starting point of the scan area, the focus (Z) stage is positioned to the best fit focus plane, an image is acquired and processed as described later, and this process is repeated for all points over the scan area. In this way, focus is maintained automatically without the need for time-consuming refocusing at points during scanning.

Figure 16:
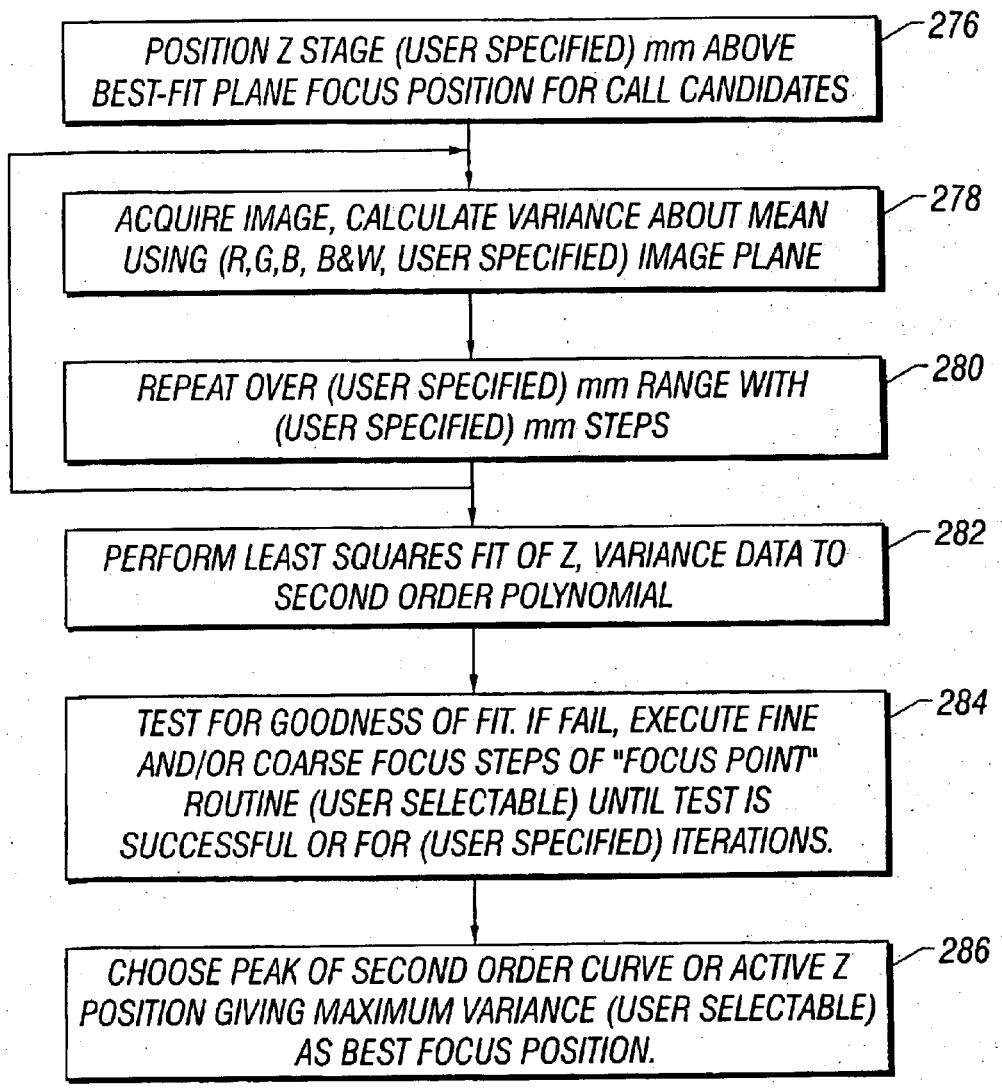
FIG. 16 is a flow diagram of a procedure for automatic focusing at a high magnification.

Prior to confirmation of cell objects at a 40× or 60× level, a refocusing operation is conducted since the use of this higher magnification requires more precise focus than the best-fit plane provides. FIG. 16 provides the flow diagram for this process. As may be seen, this process is similar to the fine focus method described earlier in that the object is to maximize the image pixel variance. This is accomplished by stepping through a range of focus positions with the Z stage at 276, 278, calculating the image variance at each position at 278, fitting a second order polynomial to these data at 282, and calculating the peak of this curve to yield an estimate of the best focus position at 284, 286. This final focusing step differs from previous ones in that the focus range and focus step sizes are smaller since this magnification requires focus settings to within 0.5 micron or better.

It should be noted that for some combinations of cell staining characteristics, improved focus can be obtained by numerically selecting the focus position that provides the largest variance, as opposed to selecting the peak of the polynomial. In such cases, the polynomial is used to provide an estimate of best focus, and a final step selects the actual Z position giving highest pixel variance. It should also be noted that if at any time during the focusing process at 40× or 60× the parameters indicate that the focus position is inadequate, the system automatically reverts to a coarse focusing process as described above with reference to FIG. 13A. This ensures that variations in specimen thickness can be accommodated in an expeditious manner.

For some biological specimens and stains, the focusing methods discussed above do not provide optimal focused results. For example, certain white blood cells known as neutrophils may be stained with Fast Red, a commonly known stain, to identify alkaline phosphatase in the cytoplasm of the cells. To further identify these cells and the material within them, the specimen may be counterstained with hemotoxylin to identify the nucleus of the cells. In cells so treated, the cytoplasm bearing alkaline phosphatase becomes a shade of red proportionate to the amount of alkaline phosphatase in the cytoplasm and the nucleus becomes blue. However, where the cytoplasm and nucleus overlap, the cell appears purple. These color combinations appear to preclude the finding of a focused Z position using the focus processes discussed above.

Figure 13B:
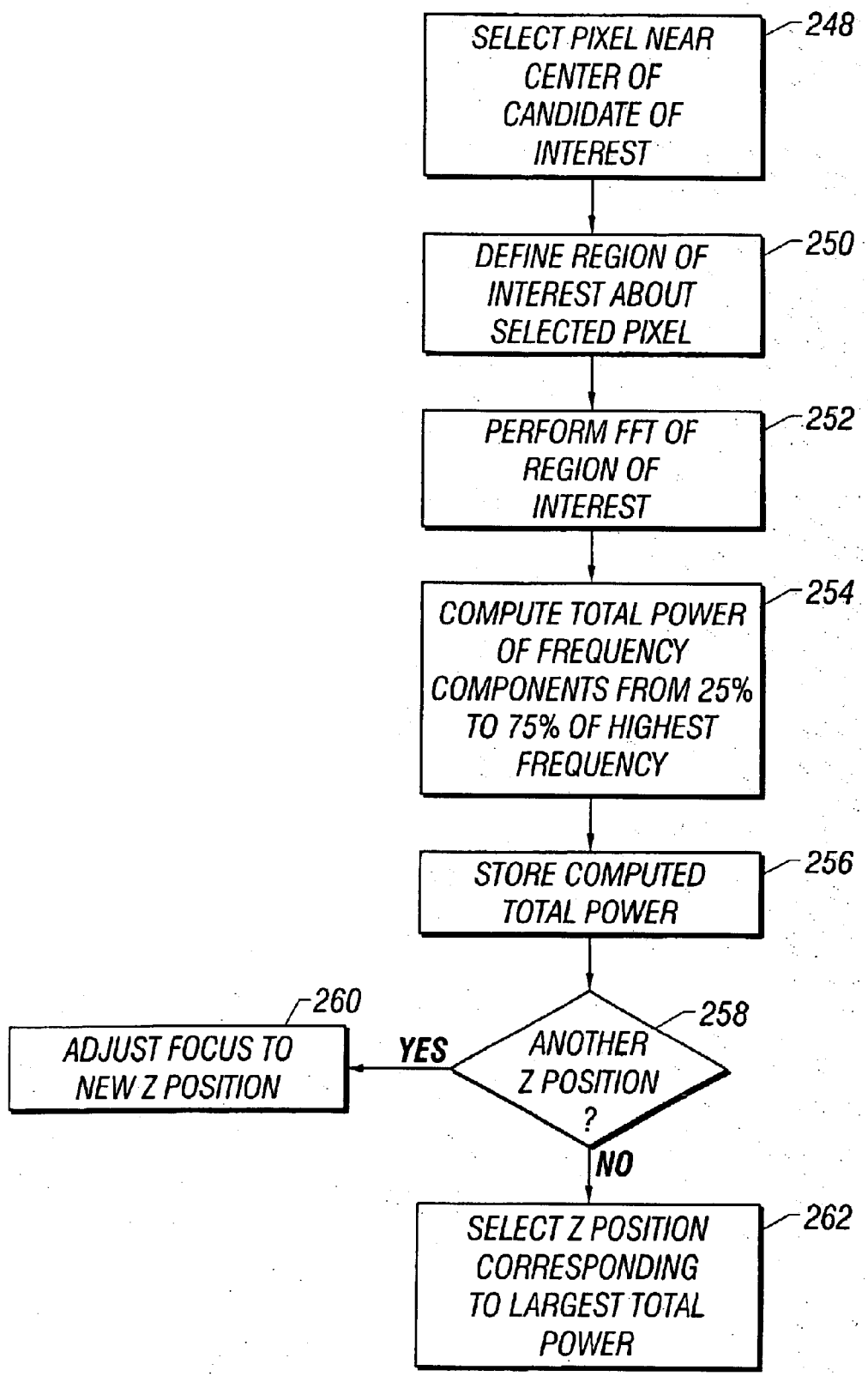
FIG. 13B is a flow diagram of a preferred procedure for determining a focal position for neutrophils stained with Fast Red and counterstained with hemotoxylin.

In an effort to find a best focal position at high magnification, a focus method, such as the one shown in FIG. 13B, may be used. That method begins by selecting a pixel near the center of a candidate object of interest (Block 248) and defining a region of interest centered about the selected pixel (Block 250). Preferably, the width of the region of interest is a number of columns which is a power of 2. This width preference arises from subsequent processing of the region of interest preferably using a one dimensional Fast Fourier Transform (FFT) technique. As is well known within, the art, processing columns of pixel values using the FFT technique is facilitated by making the number of columns to be processed a power of two. While the height of the region of interest is also a power of two in the preferred embodiment, it need not be unless a two dimensional FFT technique is used to process the region of interest.

After the region of interest is selected, the columns of pixel values are processed using the preferred one dimensional FFT to determine a spectra of frequency components for the region of interest (Block 252). The frequency spectra ranges from DC to some highest frequency component. For each frequency component, a complex magnitude is computed. Preferably, the complex magnitudes for the frequency components which range from approximately 25% of the highest component to approximately 75% of the highest component are squared and summed to determine the total power for the region of interest (Block 254). Alternatively, the region of interest may be processed with a smoothing window, such as a Hanning window, to reduce the spurious high frequency components generated by the FFT processing of the pixel values in the region of interest. Such preprocessing of the region of interest permits all complex magnitude over the complete frequency range to be squared and summed. After the power for a region has been computed and stored (Block 256), a new focal position is selected, focus adjusted (Blocks 258, 260), and the process repeated. After each focal position has been evaluated, the one having the greatest power factor is selected as the one best in focus (Block 262).

The following describes the image processing methods which are utilized to decide whether a candidate object of interest such as a stained tumor cell is present in a given image, or field, during the scanning process. Candidate objects of interest which are detected during scanning are reimaged at higher (40× or 60×) magnification, the decision confirmed, and a region of interest for this cell saved for later review by the pathologist.

The image processing includes color space conversion, low pass filtering, background suppression, artifact suppression, morphological processing, and blob analysis. One or more of these steps can optionally be eliminated. The operator is provided with an option to configure the system to perform any or all of these steps and whether to perform certain steps more than once or several times in a row. It should also be noted that the sequence of steps may be varied and thereby optimized for specific reagents or reagent combinations; however, the sequence described herein is preferred. It should be noted that the image processing steps of low pass filtering, thresholding, morphological processing, and blob analysis are generally known image processing building blocks.

Figure 17A:
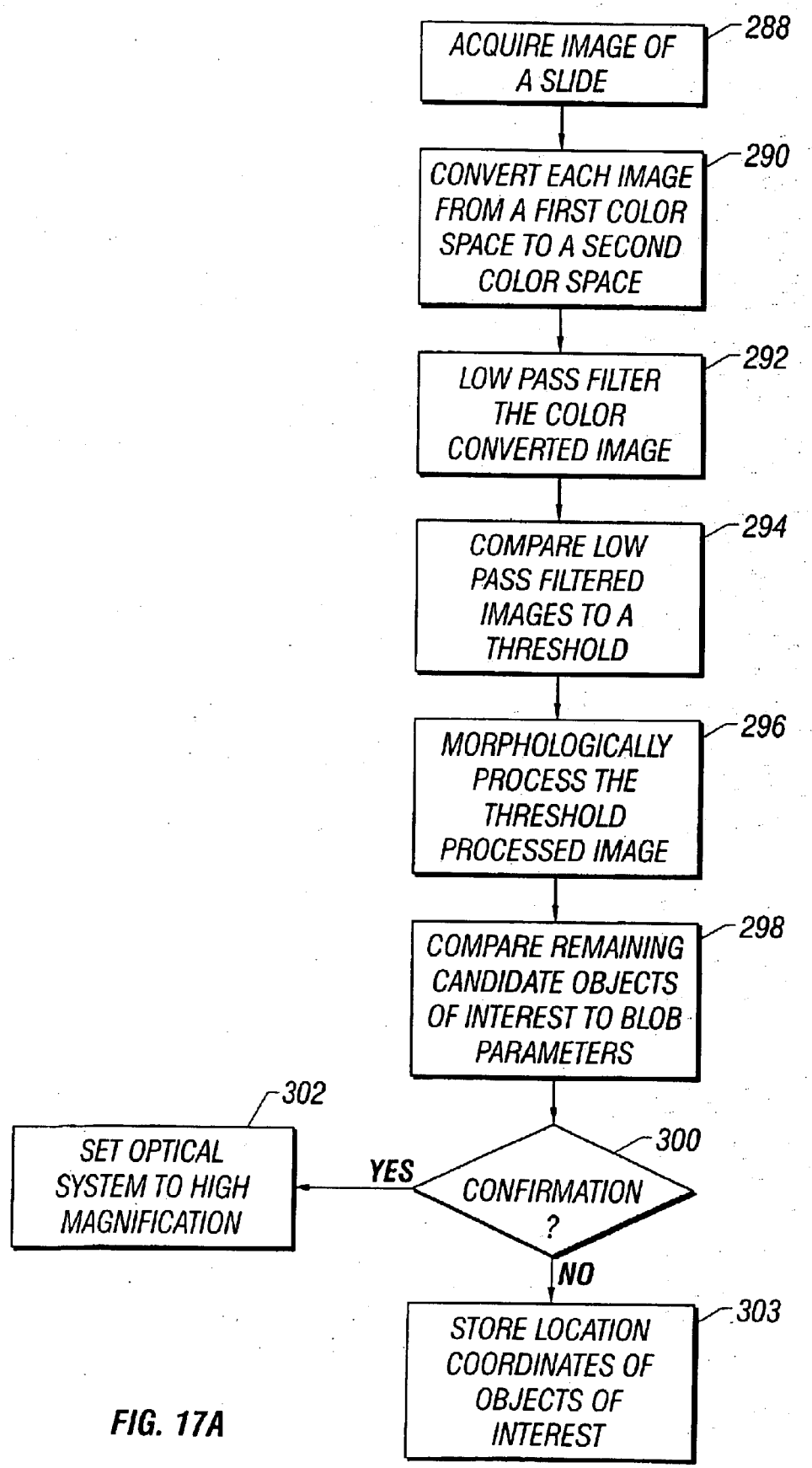
FIG. 17A is a flow diagram of an overview of the preferred process to locate and identify objects of interest in a stained biological specimen on a slide.

An overview of the preferred process is shown in FIG. 17A. The preferred process for identifying and locating candidate objects of interest in a stained biological specimen on a slide begins with an acquisition of images obtained by scanning the slide at low magnification (Block 288). Each image is then converted from a first color space to a second color space (Block 290) and the color converted image is low pass filtered (Block 292). The pixels of the low pass filtered image are then compared to a threshold (Block 294) and, preferably, those pixels having a value equal to or greater than the threshold are identified as candidate object of interest pixels and those less than the threshold are determined to be artifact or background pixels. The candidate object of interest pixels are then morphologically processed to identify groups of candidate object of interest pixels as candidate objects of interest (Block 296). These candidate objects of interest are then compared to blob analysis parameters (Block 298) to further differentiate candidate objects of interest from objects which do not conform to the blob analysis parameters and, thus, do not warrant further processing. The location of the candidate objects of interest may be stored prior to confirmation at high magnification. The process continues by determining whether the candidate objects of interest have been confirmed (Block 300). If they have not been confirmed, the optical system is set to high magnification (Block 302) and images of the slide at the locations corresponding to the candidate objects of interest identified in the low magnification images are acquired (Block 288). These images are then color converted (Block 290), low pass filtered (Block 292), compared to a threshold (Block 294), morphologically processed (Block 296), and compared to blob analysis parameters (Block 298) to confirm which candidate objects of interest located from the low magnification images are objects of interest. The coordinates of the objects of interest are then stored for future reference (Block 303).

Neural net processing schemes were not considered for the preferred embodiment for several reasons. Firstly, the preferred embodiment is optimized for "rare-event" detection, although it is not limited to this case. Since neural nets must be trained on what to look for, sometimes several thousands Of examples must be presented to the neural net for this training. This is impractical for a rare-event application. Secondly, neural net processing can be slower than "deterministic" methods, sometimes by large factors. Therefore, neural nets were not deemed appropriate for this application, although certain features of the invention may be advantageously applied to neural network systems.

In general, the candidate objects of interest, such as tumor cells, are detected based on a combination of characteristics, including size, shape, and color. The chain of decision making based on these characteristics preferably begins with a color space conversion process. The CCD camera coupled to the microscope subsystem outputs a color image comprising a matrix of 640×480 pixels. Each pixel comprises red, green and blue (RGB) signal values.

It is desirable to transform the matrix of RGB values to a different color space because the difference between candidate objects of interest and their background, such as tumor and normal cells, may be determined from their respective colors. Specimens are generally stained with one or more industry standard stains (e.g., DAB, New Fuchsin, AEC) which are "reddish" in color. Candidate objects of interest retain more of the stain and thus appear red while normal cells remain unstained. The specimens may also be counterstained with hematoxalin so the nuclei of normal cells or cells not containing an object of interest appear blue. In addition to these objects, dirt and debris can appear as black, gray, or can also be lightly stained red or blue depending on the staining procedures utilized. The residual plasma or other fluids also present on a smear may also possess some color.

In the color conversion operation, a ratio of two of the RGB signal values is formed to provide a means for discriminating color information. With three signal values for each pixel, nine different ratios can be formed:

R/R, R/G, R/B, G/G, G/B, G/R, B/B, B/G, B/R

The optimal ratio to select depends upon the range of color information expected in the slide specimen. As noted above, typical stains used for detecting candidate objects of interest such as tumor cells are predominantly red, as opposed to predominantly green or blue. Thus, the pixels of a cell of interest which has been stained contain a red component which is larger than either the green or blue components. A ratio of red divided by blue (R/B) provides a value which is greater than one for tumor cells but is approximately one for any clear or white areas on the slide. Since the remaining cells, i.e., normal cells, typically are stained blue, the R/B ratio for pixels of these latter cells yields values of less than one. The R/B ratio is preferred for clearly separating the color information typical in these applications.

Figure 17B:
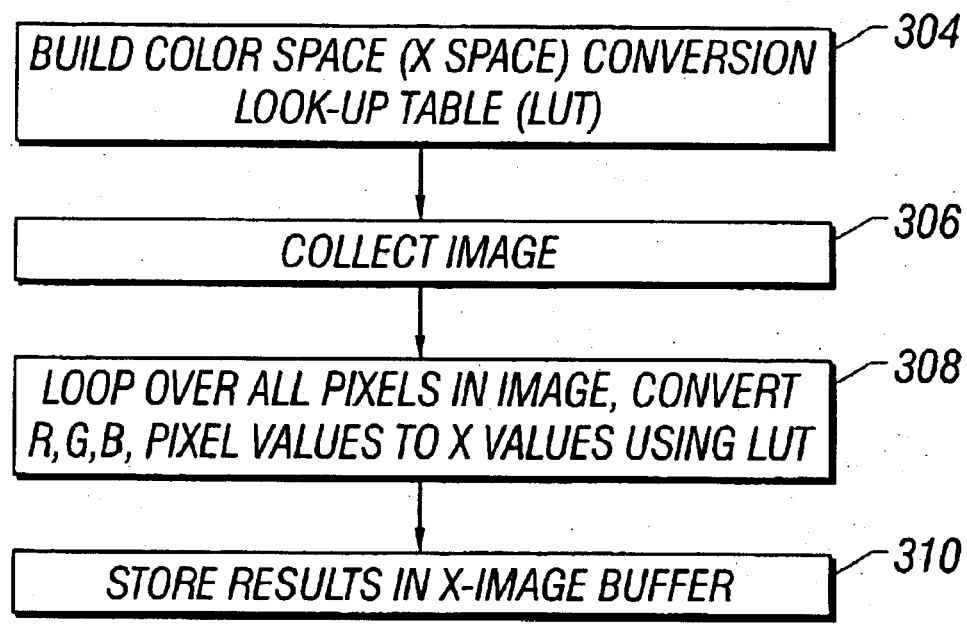
FIG. 17B is a flow diagram of a procedure for color space conversion.

FIG. 17B illustrates the flow diagram by which this conversion is performed. In the interest of processing speed, the conversion is implemented with a look up table. The use of a look up table for color conversion accomplishes three functions: 1) performing a division operation; 2) scaling the result for processing as an image having pixel values ranging from 0 to 255; and 3) defining objects which have low pixel values in each color band (R,G,B) as "black" to avoid infinite ratios (i.e., dividing by zero). These "black" objects are typically staining artifacts or can be edges of bubbles caused by pasting a coverglass over the specimen.

Once the look up table is built at 304 for the specific color ratio (i.e., choices of tumor and nucleated cell stains), each pixel in the original RGB image is converted at 308 to produce the output. Since it is of interest to separate the red stained tumor cells from blue stained normal ones, the ratio of color values is then scaled by a user specified factor. As an example, for a factor of 128 and the ratio of (red pixel value)/(blue pixel value), clear areas on the slide would have a ratio of 1 scaled by 128 for a final X value of 128. Pixels which lie in red stained tumor cells would have X value greater than 128, while blue stained nuclei of normal cells would have value less than 128. In this way, the desired objects of interest can be numerically discriminated. The resulting 640×480 pixel matrix, referred to as the X-image, is a gray scale image having values ranging from 0 to 255.

Other methods exist for discriminating color information. One classical method converts the RGB color information into another color space, such as HSI (hue, saturation, intensity) space. In such a space, distinctly different hues such as red, blue, green, yellow, may be readily separated, In addition, relatively lightly stained objects may be distinguished from more intensely stained ones by virtue of differing saturations. However, converting from RGB space to HSI space requires more complex computation. Conversion to a color ratio is faster; for example, a full image can be converted by the ratio technique of the present invention in about 30 ms while an HSI conversion can take several seconds.

In yet another approach, one could obtain color information by taking a single color channel from the camera. As an example, consider a blue channel, in which objects that are red are relatively dark. Objects which are blue, or white, are relatively light in the blue channel. In principle, one could take a single color channel, and simply set a threshold wherein everything darker than some threshold is categorized as a candidate object of interest, for example, a tumor cell, because it is red and hence dark in the channel being reviewed. However, one problem with the single channel approach occurs where illumination is not uniform. Non-uniformity of illumination results in non-uniformity across the pixel values in any color channel, for example, tending to peak in the middle of the image and dropping off at the edges where the illumination falls off. Performing thresholding on this non-uniform color information runs into problems, as the edges sometimes fall below the threshold, and therefore it becomes more difficult to pick the appropriate threshold level. However, with the ratio technique, if the values of the red channel fall off from center to edge, then the values of the blue channel also fall off center to edge, resulting in a uniform ratio. Thus, the ratio technique is more immune to illumination non-uniformities.

As previously described, the color conversion scheme is relatively insensitive to changes in color balance, i.e., the relative outputs of the red, green, and blue channels. However, some control is necessary to avoid camera saturation, or inadequate exposures in any one of the color bands. This color balancing is performed automatically by utilizing a calibration slide consisting of a clear area, and a "dark" area having a known optical transmission or density. The system obtains images from the clear and "dark" areas, calculates "white" and "black" adjustments for the image processor 25, and thereby provides correct color balance.

In addition to the color balance control, certain mechanical alignments are automated in this process. The center point in the field of view for the various microscope objectives as measured on the slide can vary by several (or several tens of) microns. This is the result of slight variations in position of the microscope objectives 44a as determined by the turret 44 (FIG. 4), small variations in alignment of the objectives with respect to the system optical axis, and other factors. Since it is desired that each microscope objective be centered at the same point, these mechanical offsets must be measured and automatically compensated.

This is accomplished by imaging a test slide which contains a recognizable feature or mark. An image of this pattern is obtained by the system with a given objective, and the position of the mark determined. The system then rotates the turret to the next lens objective, obtains an image of the test object, and its position is redetermined. Apparent changes in position of the test mark are recorded for this objective. This process is continued for all objectives.

Once these spatial offsets have been determined, they are automatically compensated for by moving the stage 38 by an equal (but opposite) amount of offset during changes in objective. In this way, as different lens objectives are selected, there is no apparent shift in center point or area viewed.

A low pass filtering process precedes thresholding. An objective of thresholding is to obtain a pixel image matrix having only candidate objects of interest, such as tumor cells above a threshold level and everything else below it. However, an actual acquired image will contain noise. The noise can take several forms, including white noise and artifacts. The microscope slide can have small fragments of debris that pick up color in the staining process and these are known as artifacts. These artifacts are generally small and scattered areas, on the order of a few pixels, which are above the threshold. The purpose of low pass filtering is to essentially blur or smear the entire color converted image. The low pass filtering process will smear artifacts more than larger objects of interest such as tumor cells and thereby eliminate or reduce the number of artifacts that pass the thresholding process. The result is a cleaner thresholded image downstream.

In the low pass filter process, a 3×3 matrix of coefficients is applied to each pixel in the 640×480x-image. A preferred coefficient matrix is as follows:

$$\begin{bmatrix} 1/9 & 1/9 & 1/9 \\ 1/9 & 1/9 & 1/9 \\ 1/9 & 1/9 & 1/9 \end{bmatrix}$$

At each pixel location, a 3×3 matrix comprising the pixel of interest and its neighbors is multiplied by the coefficient matrix and summed to yield a single value for the pixel of interest. The output of this spatial convolution process is again a 640×480 matrix.

As an example, consider a case where the center pixel and only the center pixel, has a value of 255 and each of its other neighbors, top left, top, top right and so forth, have values of 0. This singular white pixel case corresponds to a small object. The result of the matrix multiplication and addition using the coefficient matrix is a value of $\frac{1}{9}$ (255) or 28 for the center pixel, a value which is below the nominal threshold of 128. Now consider another case in which all the pixels have a value of 255 corresponding to a large object. Performing the low pass filtering operation on a 3×3 matrix for this case yields a value of 255 for the center pixel. Thus, large objects retain their values while small objects are reduced in amplitude or eliminated. In the preferred method of operation, the low pass filtering process is performed on the X image twice in succession.

In order to separate objects of interest, such as a tumor cell in the x image from other objects and background, a thresholding operation is performed designed to set pixels within cells of interest to a value of 255, and all other areas to 0. Thresholding ideally yields an image in which cells of interest are white and the remainder of the image is black. A problem one faces in thresholding is where to set the threshold level. One cannot simply assume that cells of interest are indicated by any pixel value above the nominal threshold of 128. A typical imaging system may use an incandescent halogen light bulb as a light source. As the bulb ages, the relative amounts of red and blue output can change. The tendency as the bulb ages is for the blue to drop off more than the red and the green. To accommodate for this light source variation over time, a dynamic thresholding process is used whereby the threshold is adjusted dynamically for each acquired image. Thus, for each 640×480 image, a single threshold value is derived specific to that image.

Figure 18:
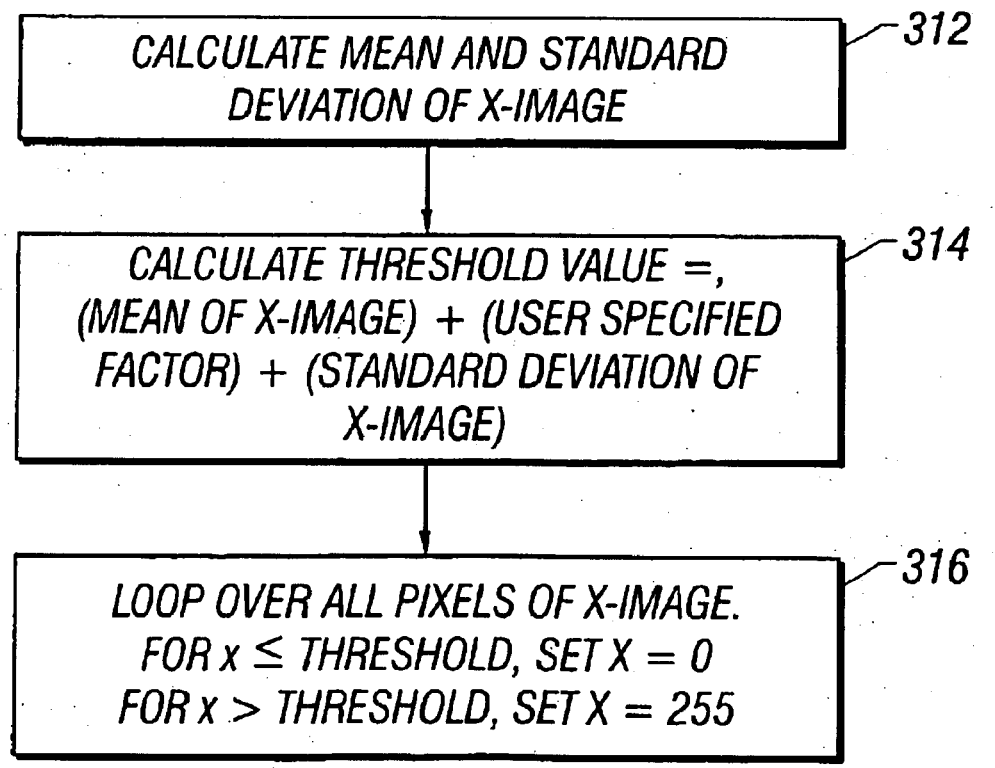
FIG. 18 is a flow diagram of a procedure for background suppression via dynamic thresholding.

As shown in FIG. 18, the basic method is to calculate, for each field, the mean X value, and the standard deviation about this mean at 312. The threshold is then set at 314 to the mean plus an amount defined by the product of a (user specified) factor and the standard deviation of the color converted pixel values. The standard deviation correlates to the structure and number of objects in the image. Preferably, the user specified factor is in the range of approximately 1.5 to 2.5. The factor is selected to be in the lower end of the range for slides in which the stain has primarily remained within cell boundaries and the factor is selected to be in the upper end of the range for slides in which the stain is pervasively present throughout the slide. In this way, as areas are encountered on the slide with greater or lower background intensities, the threshold may be raised or lowered to help reduce background objects. With this method, the threshold changes in step with the aging of the light source such that the effects of the aging are cancelled out. The image matrix resulting at 316 from the thresholding step is a binary image of black (O) and white (255) pixels.

As is often the case with thresholding operations such as that described above, some undesired areas will lie above the threshold value due to noise, small stained cell fragments, and other artifacts. It is desired and possible to eliminate these artifacts by virtue of their small size compared with legitimate cells of interest. Morphological processes are utilized to perform this function.

Morphological processing is similar to the low pass filter convolution process described earlier except that it is applied to a binary image. Similar to spatial convolution, the morphological process traverses an input image matrix, pixel by pixel, and places the processed pixels in an output matrix. Rather than calculating a weighted sum of neighboring pixels as in the low pass convolution process, the morphological process uses set theory operations to combine neighboring pixels in a nonlinear fashion.

Erosion is a process whereby a single pixel layer is taken away from the edge of an object. Dilation is the opposite process which adds a single pixel layer to the edges of an object. The power of morphological processing is that it provides for further discrimination to eliminate small objects that have survived the thresholding process and yet are not likely tumor cells. The erosion and dilation processes that make up a morphological "open" preferably make small objects disappear yet allows large objects to remain. Morphological processing of binary images is described in detail in "Digital Image Processing", pages 127–137, G. A. Baxes, John Wiley & Sons, (1994).

Figure 19:
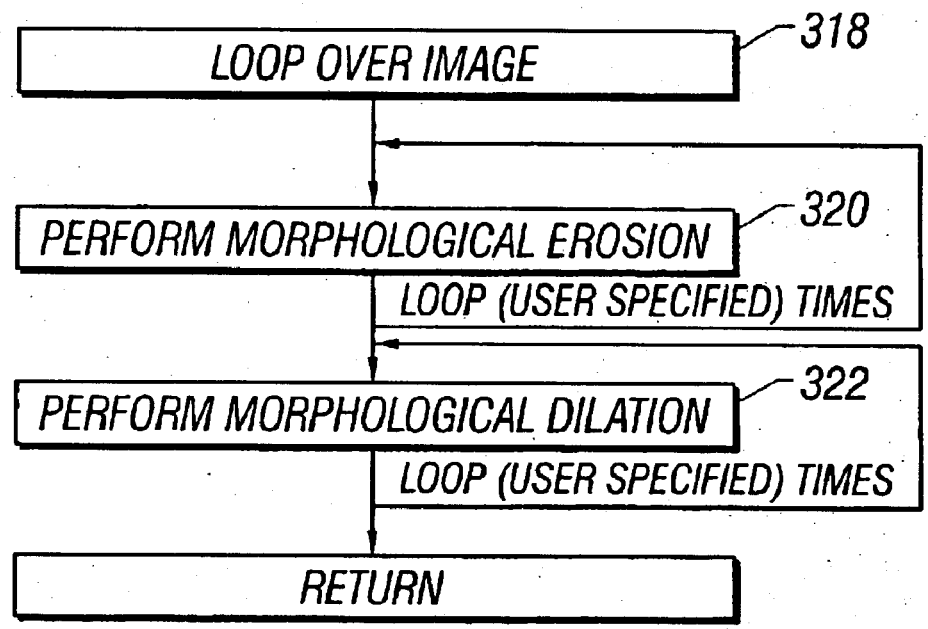
FIG. 19 is a flow diagram of a procedure for morphological processing.

FIG. 19 illustrates the flow diagram for this process. As shown here, a morphological "open" process performs this suppression. A single morphological open consists of a single morphological erosion 320 followed by a single morphological dilation 322. Multiple "opens" consist of multiple erosions followed by multiple dilations. In the preferred embodiment, one or two morphological opens are found to be suitable.

At this point in the processing chain, the processed image contains thresholded objects of interest, such as tumor cells (if any were present in the original image), and possibly some residual artifacts that were too large to be eliminated by the processes above.

Figure 20:
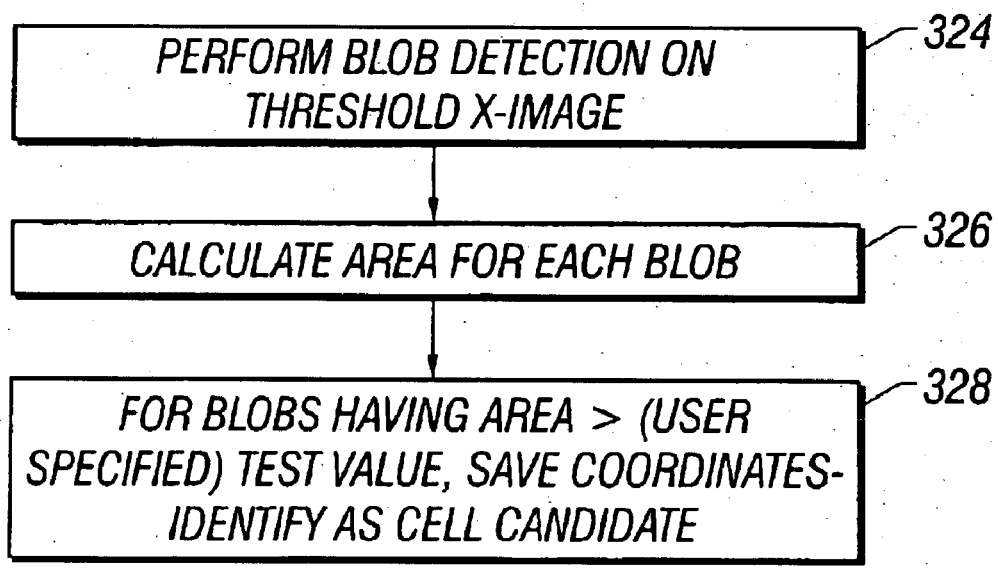
FIG. 20 is a flow diagram of a procedure for blob analysis.

FIG. 20 provides a flow diagram illustrating a blob analysis performed to determine the number, size, and location of objects in the thresholded image. A blob is defined as a region of connected pixels having the same "color", in this case, a value of 255. Processing is performed over the entire image to determine the number of such regions at 324 and to determine the area and x,y coordinates for each detected blob at 326.

Comparison of the size of each blob to a known minimum area at 328 for a tumor cell allows a refinement in decisions about which objects are objects of interest, such as tumor cells, and which are artifacts. The location (x,y coordinates) of objects identified as cells of interest in this stage are saved for the final 40× reimaging step described below. Objects not passing the size test are disregarded as artifacts.

Figure 21:
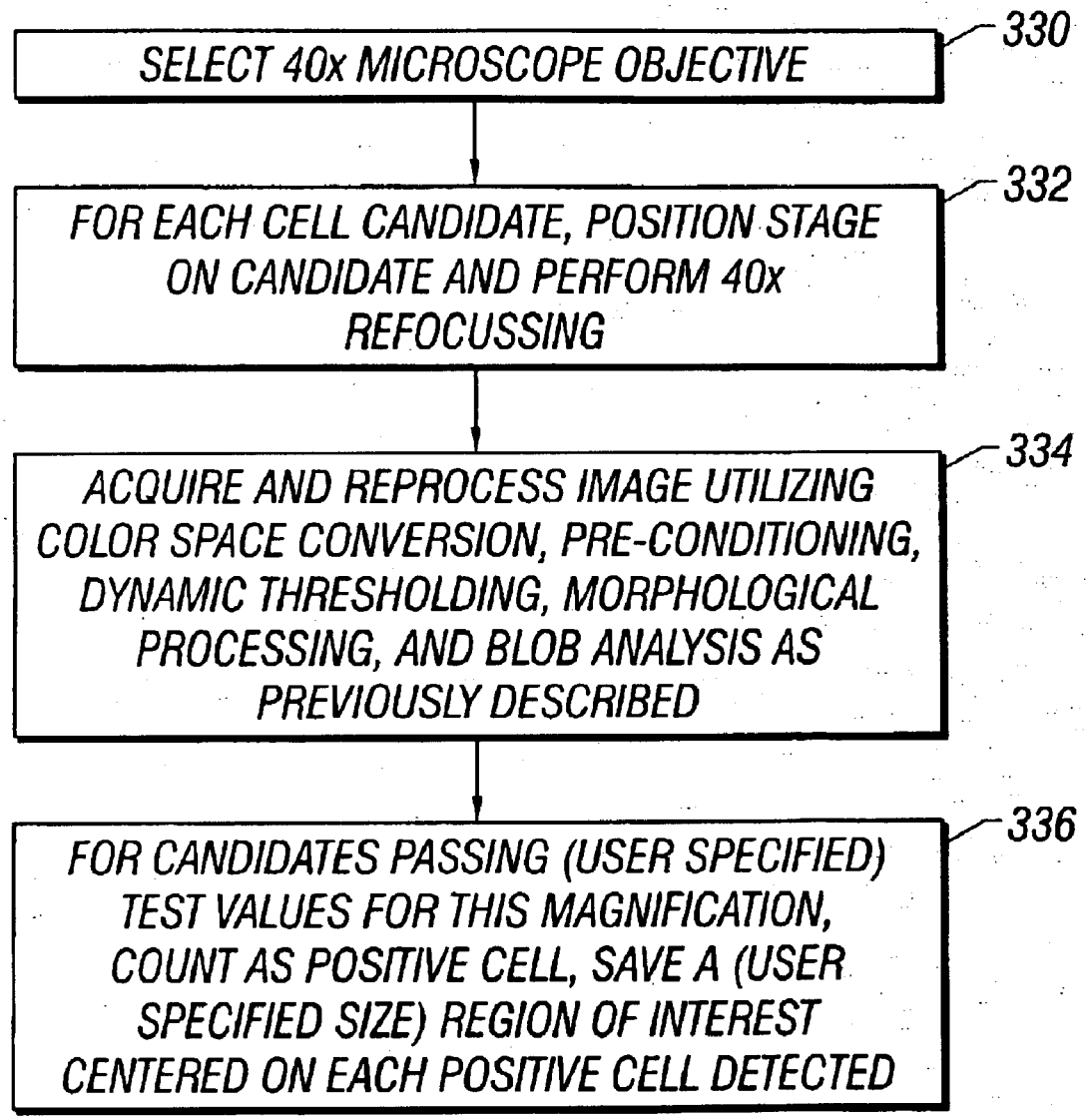
FIG. 21 is a flow diagram of a procedure for image processing at a high magnification.

The processing chain described above identifies objects at the scanning magnification as cells of interest candidates. As illustrated in FIG. 21, at the completion of scanning, the system switches to the 40× magnification objective at 330, and each candidate is reimaged to confirm the identification 332. Each 40× image is reprocessed at 334 using the same steps as described above but with test parameters suitably modified for the higher magnification (e.g. area). At 336, a region of interest centered on each confirmed cell is saved to the hard drive for review by the pathologist.

Figure 22:
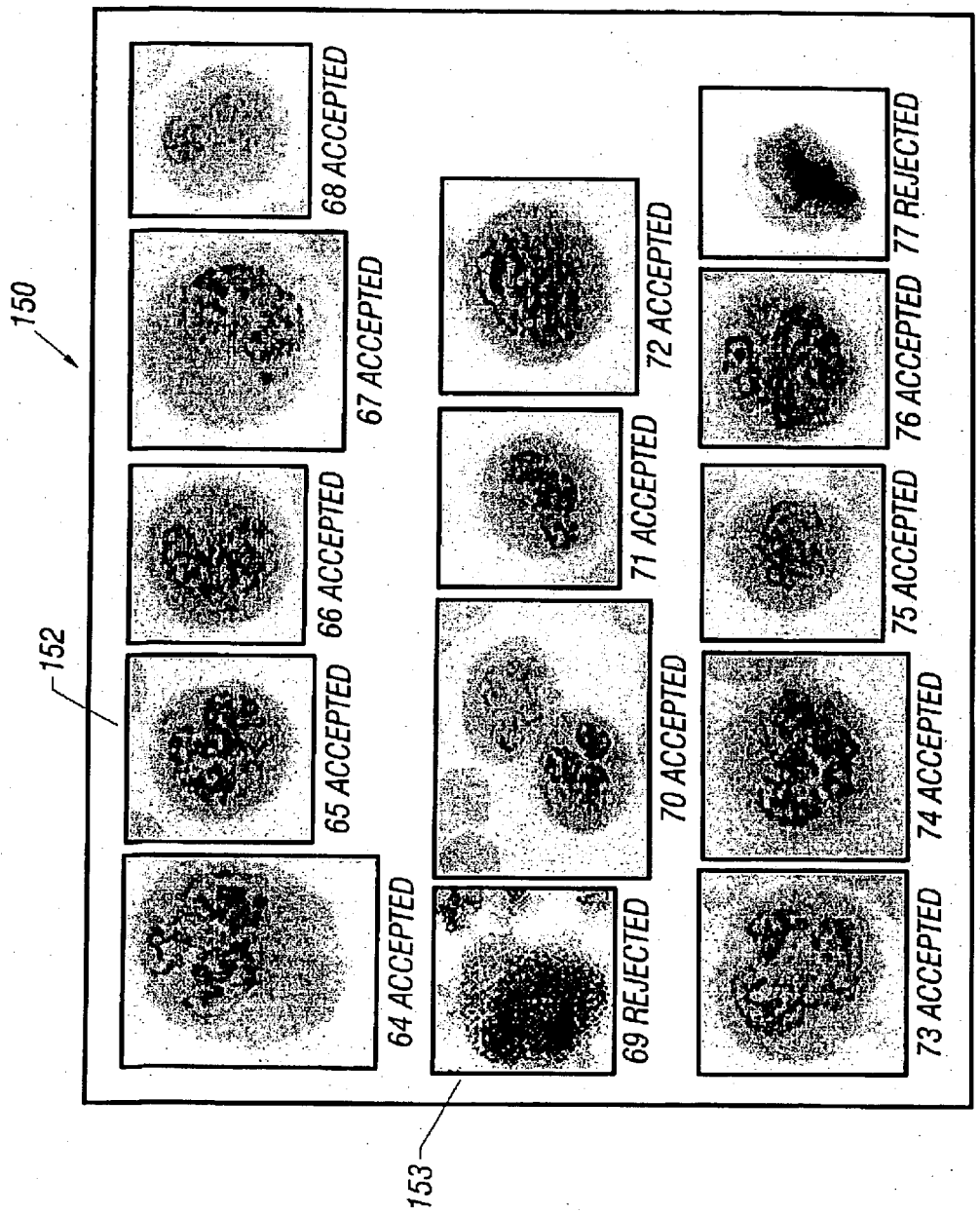
FIG. 22 illustrates a mosaic of cell images produced by the apparatus.

As noted earlier, a mosaic of saved images is made available for viewing by the pathologist. As shown in FIG. 22, a series of images of cells which have been confirmed by the image analysis is presented in the mosaic 150. The pathologist can then visually inspect the images to make a determination whether to accept (152) or reject (153) each cell image. Such a determination can be noted and saved with the mosaic of images for generating a printed report.

In addition to saving the image of the cell and its region, the cell coordinates are saved should the pathologist wish to directly view the cell through the oculars or on the image monitor. In this case, the pathologist reloads the slide carrier, selects the slide and cell for review from a mosaic of cell images, and the system automatically positions the cell under the microscope for viewing.

Figure 23:
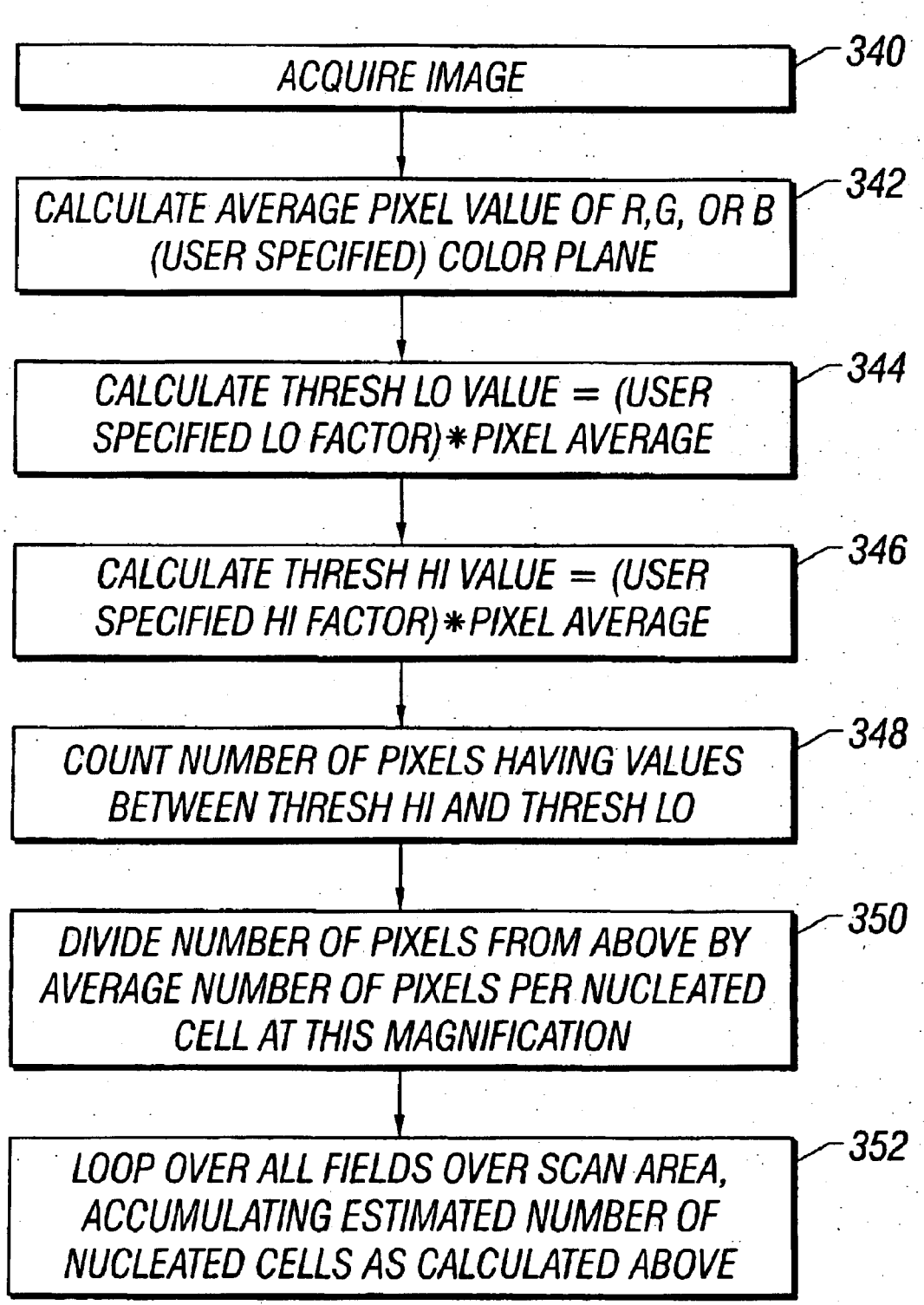
FIG. 23 is a flow diagram of a procedure for estimating the number of nucleated cells in a scan area.

It has been found that normal cells whose nuclei have been stained with hematoxylin are often quite numerous, numbering in the thousands per 10× image. Since these cells are so numerous, and since they tend to clump, counting each individual nucleated cell would add an excessive processing burden, at the expense of speed, and would not necessarily provide an accurate count due to clumping. The apparatus performs an estimation process in which the total area of each field that is stained hematoxylin blue is measured and this area is divided by the average size of a nucleated cell. FIG. 23 outlines this process.

In this process, a single color band (the red channel provides the best contrast for blue stained nucleated cells) is processed by calculating the average pixel value for each field at 342, establishing two threshold values (high and low) as indicated at 344, 346, and counting the number of pixels between these two values at 348. In the absence of dirt, or other opaque debris, this provides a count of the number of predominantly blue pixels. By dividing this value by the average area for a nucleated cell at 350, and looping over all fields at 352, an approximate cell count is obtained. Preliminary testing of this process indicates an accuracy with +/−15%. It should be noted that for some slide preparation techniques, the size of nucleated cells can be significantly larger than the typical size. The operator can select the appropriate nucleated cell size to compensate for these characteristics.

As with any imaging system, there is some loss of modulation transfer (i.e. contrast) due to the modulation transfer function (MTF) characteristics of the imaging optics, camera, electronics, and other components. Since it is desired to save "high quality" images of cells of interest both for pathologist review and for archival purposes, it is desired to compensate for these MTF losses.

An MTF compensation, or MTFC, is performed as a digital process applied to the acquired digital images. A digital filter is utilized to restore the high spatial frequency content of the images upon storage, while maintaining low noise levels. With this MTFC technology, image quality is enhanced, or restored, through the use of digital processing methods as opposed to conventional oil-immersion or other hardware based methods. MTFC is described further in "The Image Processing Handbook," pages 225 and 337, J. C. Rues, CRC Press (1995).

Figure 24A:
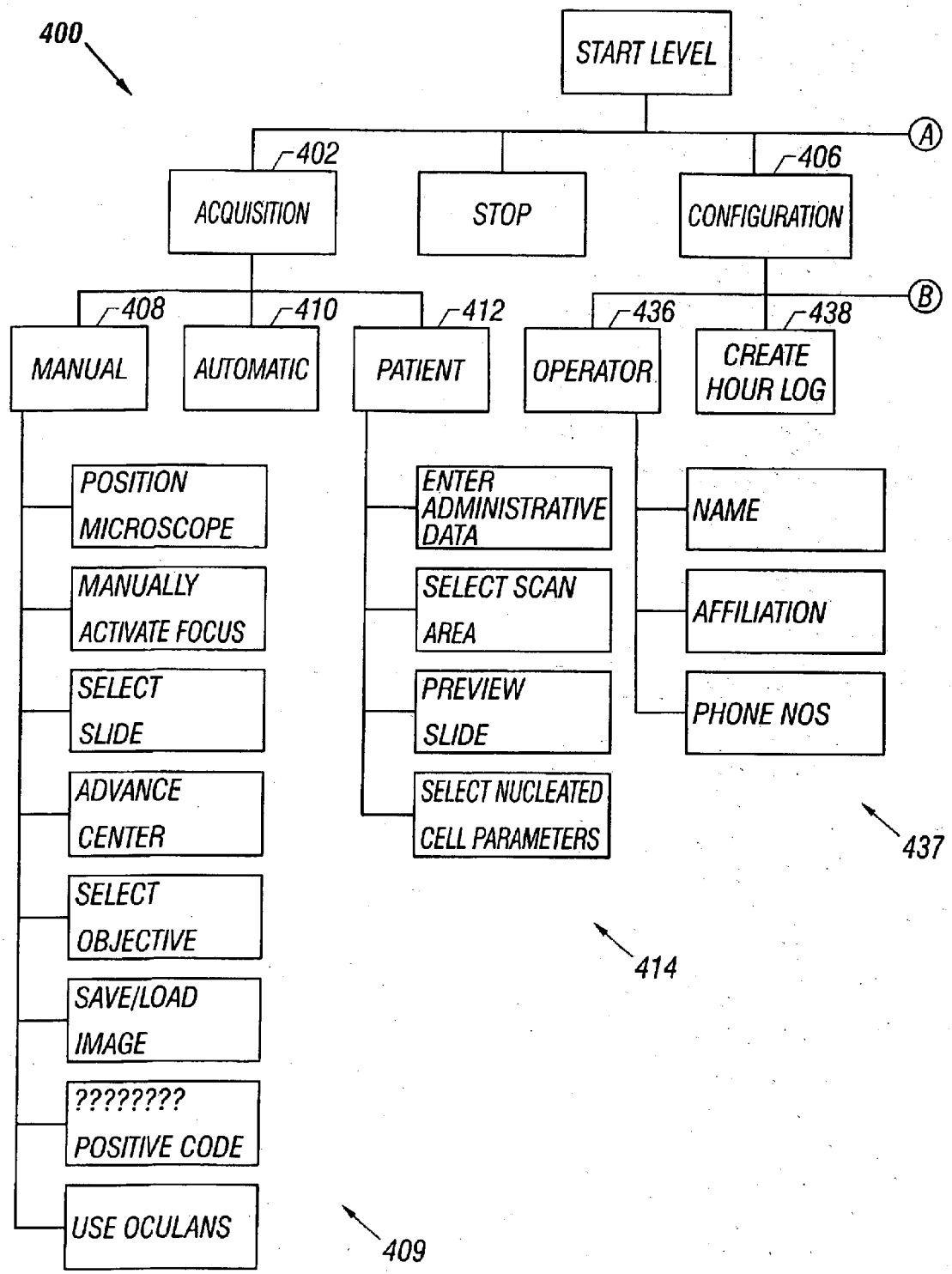
FIGS. 24A and 24B illustrate the apparatus functions available in a user interface of the apparatus.
Figure 24B:
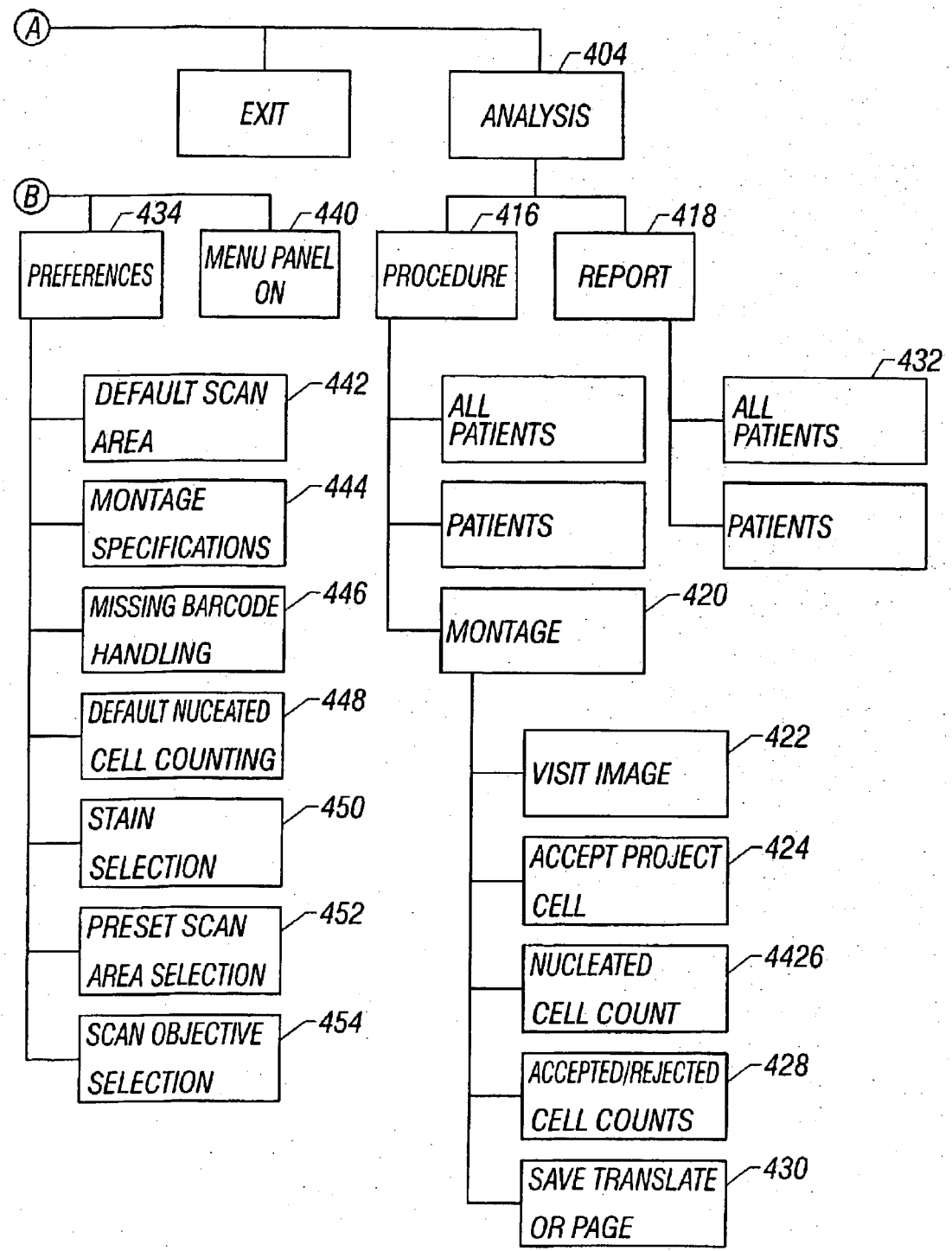

Referring to FIG. 24, the functions available in a user interface of the apparatus 10 are shown. From the user interface, which is presented graphically on computer monitor 26, an operator can select among apparatus functions which include acquisition 402, analysts 404, and system configuration 406. At the acquisition level 402, the operator can select between manual 408 and automatic 410 modes of operation. In the manual mode, the operator is presented with manual operations 409. Patient information 414 regarding an assay can be entered at 412.

In the analysis level 404, review 416 and report 418 functions are made available. At the review level 416, the operator can select a montage function 420. At this montage level, a pathologist can perform diagnostic review functions including visiting an image 422, accept/reject of cells 424, nucleated cell counting 426, accept/reject of cell counts 428, and saving of pages at 430. The report level 418 allows an operator to generate patient reports 432.

In the configuration level 406, the operator can select to configure preferences at 434, input operator information 437 at 436, create a system log at 438, and toggle a menu panel at 440. The configuration preferences include scan area selection functions at 442, 452; montage specifications at 444, bar code handling at 446, default cell counting at 448, stain selection at 450, and scan objective selection at 454.

Equivalents

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of automated sample analysis comprising:

identifying a size, shape, and location of a scan area on a slide, wherein the scan area comprises a sample;

scanning a the scan area in a raster fashion using an automated microscope system;

obtaining a plurality of images of adjacent fields of view at each scan location to yield a plurality of adjacent images comprising the sample;

digitizing the images; and processing the images to identify an object of interest by transforming substantially all pixels of the images from a first color space to a second color space.

2. The method of claim 1, wherein the identifying of the size, shape and location is comprises:

acquiring one or more images of the slide at a low magnification;

analyzing texture information of the one or more images to detect the edges of the sample; and storing the locations corresponding to the detected edges to define the scan area.

3. The method of claim 1, wherein the processing of the images comprises:

identifying the object of interest from said transformed pixels in said second color space with reference to a predetermined threshold.

4. The method of claim 1, wherein the first color space includes red, green, and blue components for each pixel.

5. The method of claim 1, wherein the processing comprises:

(a) transforming pixels of the images in the first color space to the second color space to differentiate candidate object of interest pixels from background pixels; and (b) identifying the objects of interest from the candidate object of interest pixels in the second color space.

6. The method of claim 1, wherein the first color space includes red, green, and blue components for each pixel and the transforming step includes comparing pixel values for a single components for each pixel to a threshold to identify pixels having a component value equal to or greater than said threshold as candidate object of interests pixels and pixels having a component value less than the threshold as background pixels.

* * * * *